United States Patent
Lussier et al.

(10) Patent No.: US 11,385,712 B2
(45) Date of Patent: Jul. 12, 2022

(54) PUPIL TRACKING SYSTEM AND METHOD, AND DIGITAL DISPLAY DEVICE AND DIGITAL IMAGE RENDERING SYSTEM AND METHOD USING SAME

(71) Applicant: EVOLUTION OPTIKS LIMITED, Christ Church (BB)

(72) Inventors: Guillaume Lussier, Montreal (CA); Khaled El-Monajjed, Montreal (CA); Daniel Gotsch, Redwood City, CA (US)

(73) Assignee: Evolution Optiks Limited, Christ Church (BB)

( * ) Notice: Subject to any disclaimer, the term of this patent is extended or adjusted under 35 U.S.C. 154(b) by 0 days.

(21) Appl. No.: 17/239,385

(22) Filed: Apr. 23, 2021

(65) Prior Publication Data
US 2021/0271319 A1    Sep. 2, 2021

Related U.S. Application Data

(63) Continuation of application No. PCT/IB2020/053035, filed on Mar. 31, 2020.
(Continued)

(30) Foreign Application Priority Data

Apr. 1, 2019  (CA) ................................ CA 3038584

(51) Int. Cl.
   *G06F 3/01*     (2006.01)
   *G09G 3/02*     (2006.01)
(52) U.S. Cl.
   CPC ............... *G06F 3/013* (2013.01); *G09G 3/02* (2013.01); *G09G 2320/0261* (2013.01)

(58) Field of Classification Search
   CPC .. G06F 3/013; G09G 3/02; G09G 2320/0261; G02B 27/017; G02B 27/0172;
   (Continued)

(56) References Cited

U.S. PATENT DOCUMENTS 6,669,651 B1 * 12/2003 Fukushima ............ A61B 3/112
                                                600/558
7,572,008 B2    8/2009 Elvesjo et al.
(Continued)

FOREIGN PATENT DOCUMENTS

WO       2018000020 A1    1/2018

OTHER PUBLICATIONS

Fuhl W. et al. "PupilNet v2.0: Convolutional Neural Network for CPU based real time Robust Pupil Detection", arXiv: 1711.00112, 2017.
(Continued)

*Primary Examiner* — Richard J Hong
(74) *Attorney, Agent, or Firm* — Knobbe, Martens, Olson & Bear, LLP

(57) ABSTRACT

Described are various embodiments of a pupil tracking system and method, and digital display device and digital image rendering system and method using same. In one embodiment, a computer-implemented method for dynamically adjusting rendering of a digital image using a light field display comprises: sequentially acquiring a user pupil location; digitally computing a velocity thereof over time; digitally comparing the velocity with a designated threshold pupil velocity; digitally rendering the digital image via the light field display in accordance with a maintained light field viewing zone geometry digitally defined in respect of a previously acquired user pupil location unless the velocity is above the designated threshold pupil velocity.

27 Claims, 13 Drawing Sheets

Related U.S. Application Data

(60) Provisional application No. 62/929,599, filed on Nov. 1, 2019.

(58) Field of Classification Search
CPC ............... G02B 3/0006; G02B 26/101; G06K 9/00617; H04N 5/23229; H04N 13/307; A61B 3/112
See application file for complete search history.

(56) References Cited

U.S. PATENT DOCUMENTS

| | | | |
|---|---|---|---|
| 8,066,375 B2 | 11/2011 | Skogö et al. | |
| 8,120,577 B2 | 2/2012 | Bouvin et al. | |
| 8,342,687 B2 | 1/2013 | Blixt et al. | |
| 8,824,779 B1 | 9/2014 | Smyth | |
| 8,885,882 B1 | 11/2014 | Yin et al. | |
| 2014/0327771 A1* | 11/2014 | Malachowsky | G02B 3/0006 348/148 |
| 2015/0223684 A1 | 8/2015 | Hinton | |
| 2015/0338915 A1* | 11/2015 | Publicover | G02B 27/017 345/633 |
| 2016/0062459 A1* | 3/2016 | Publicover | H04N 5/23229 345/633 |
| 2016/0085302 A1* | 3/2016 | Publicover | G02B 27/0172 345/633 |
| 2016/0148050 A1 | 5/2016 | Lee | |
| 2016/0166146 A1* | 6/2016 | Sarkar | G02B 26/101 351/210 |
| 2016/0274660 A1* | 9/2016 | Publicover | G06K 9/00617 |
| 2016/0335475 A1 | 11/2016 | Krenzer et al. | |
| 2017/0011492 A1 | 1/2017 | Thunström et al. | |
| 2017/0353717 A1* | 12/2017 | Zhou | H04N 13/307 |
| 2018/0008141 A1 | 1/2018 | Krueger | |
| 2018/0011533 A9 | 1/2018 | Marggraff et al. | |
| 2018/0136722 A1 | 5/2018 | Mallinson | |
| 2018/0143684 A1 | 5/2018 | Kuldkepp et al. | |
| 2018/0181809 A1 | 6/2018 | Ranjan et al. | |
| 2018/0206771 A1 | 7/2018 | Kobetski et al. | |
| 2018/0224933 A1 | 8/2018 | George-Svahn et al. | |

OTHER PUBLICATIONS

Kar A. & Corcoran P., "A Review and Analysis of Eye-Gaze Estimation Systems, Algorithms and Performance Evaluation Methods in Consumer Platforms", IEEE Access, vol. 5, pp. 16495-16519, 2017.

Kim M., Wang O., Ng N., Convolutional Neural Network Architectures for Gaze Estimation on Mobile Device, Course Project Report, CS231n: Convolutional Neural Networks for Visual Recognition, 2017.

Koko & Florez "Cost Effective IR-Free Eye Tracking on Mobile Device", Senior Research Proposal, Department of Mathematics and Computer Science, Stetson University, Florida, 2016.

Krafka K. et al. "Eye Tracking for Everyone", 2016 IEEE Conference on Computer Vision and Pattern Recognition, IEEE, pp. 2176-2184, 2016.

Naqvi R. A. et al., "Deep Learning-Based Gaze Detection System for Automobile Drivers Using a NIR Camera Sensor", Sensor, doi: 10.3390/s18020456, pp. 1-34, 2018.

Santini T. et al. "PuRe: Robust pupil detection for real-time pervasive eye tracking", arXiv:1712.08900v1, 2017.

Swirski et al. "Robust real-time pupil tracking in highly off-axis images", Proceedings of the Symposium on Eye Tracking Research and Applications, pp. 173-176, 2012.

\* cited by examiner

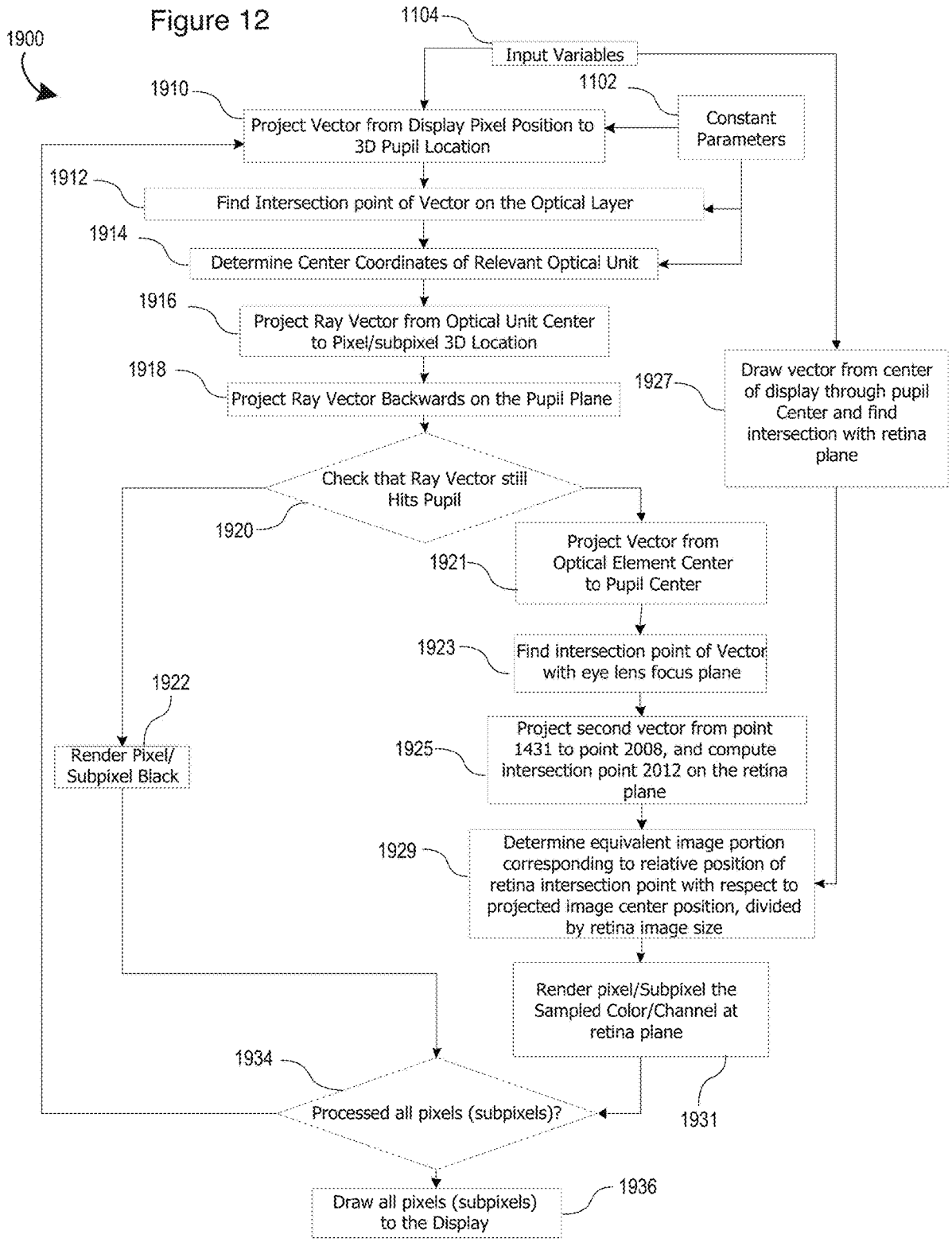

PUPIL TRACKING SYSTEM AND METHOD, AND DIGITAL DISPLAY DEVICE AND DIGITAL IMAGE RENDERING SYSTEM AND METHOD USING SAME

CROSS REFERENCE TO RELATED APPLICATIONS

This application is a Continuation of International Application No. PCT/IB2020/053035 filed Mar. 31, 2020, which claims priority to Canadian Patent Application No. 3,038,584 filed Apr. 1, 2019, and to U.S. Provisional Patent Application No. 62/929,599 filed Nov. 1, 2019, the entire disclosure of each of which are incorporated herein by reference.

FIELD OF THE DISCLOSURE

The present disclosure relates to eye tracking and digital displays, and, in particular, to a pupil tracking system and method, and digital display device and digital image rendering system and method using same.

BACKGROUND

Gaze tracking technologies are currently being applied in different fields, for example, in the context of display content engagement tracking, or in tracking a user's attention and/or distraction in different contexts such as while driving a vehicle. One may generally define two broad categories of gaze tracking technologies. The first category generally relies on projecting near-IR light on a user's face and detecting corneo-scleral reflections (i.e. glints) on the user's eye to do so-called bright and/or dark pupil tracking. Different products of this type are available, for example TOBII (http://www.tobii.com) provides a range of products using such technology. Another broad category includes computer vision methods that rely on extracting facial features from digital images or videos. Examples of products for computer vision facial feature extraction include Face++ (https://www.faceplusplus.com) or the open source facial feature extraction library OpenFace (https://github.com/TadasBaltrusaitis/OpenFace).

Using these techniques, a user's gaze direction can be monitored in real-time and put in context to monitor what draw's the user's attention over time.

This background information is provided to reveal information believed by the applicant to be of possible relevance. No admission is necessarily intended, nor should be construed, that any of the preceding information constitutes prior art or forms part of the general common knowledge in the relevant art.

SUMMARY

The following presents a simplified summary of the general inventive concept(s) described herein to provide a basic understanding of some aspects of the disclosure. This summary is not an extensive overview of the disclosure. It is not intended to restrict key or critical elements of embodiments of the disclosure or to delineate their scope beyond that which is explicitly or implicitly described by the following description and claims.

In accordance with one aspect, there is provided a computer-implemented method, automatically implemented by one or more digital processors, for dynamically adjusting a digital image to be rendered on a digital display based on a corresponding viewer pupil location, the method comprising: sequentially acquiring a user pupil location; digitally computing from at least some said sequentially acquired user pupil location an estimated physical trajectory and/or velocity of said user pupil location over time; digitally predicting from said estimated physical trajectory and/or velocity a predicted user pupil location for a projected time; and digitally adjusting the digital image to be rendered at said projected time based on said predicted user pupil location.

In accordance with another aspect, there is provided a computer-readable medium having instructions stored thereon to be automatically implemented by one or more processors to dynamically adjust a digital image to be rendered based on a corresponding viewer pupil location by: sequentially acquiring a user pupil location; digitally computing from at least some said sequentially acquired user pupil location an estimated physical trajectory and/or velocity of said user pupil location over time; digitally predicting from said estimated trajectory and/or velocity a predicted user pupil location for a projected time; and digitally adjusting the digital image to be rendered at said projected time based on said predicted user pupil location.

In accordance with another aspect, there is provided a digital display device operable to automatically adjust a digital image to be rendered thereon, the device comprising: a digital display medium; a hardware processor; and a pupil tracking engine operable by said hardware processor to automatically: receive as input sequential user pupil locations; digitally compute from said sequential user pupil locations an estimated physical trajectory of said user pupil location over time; and digitally predict from said estimated trajectory a predicted user pupil location for a projected time; wherein said hardware processor is operable to adjust the digital image to be rendered via said digital display medium at said projected time based on said predicted user pupil location.

In accordance with another aspect, there is provided a computer-implemented method, automatically implemented by one or more digital processors, for dynamically adjusting rendering of a digital image using a light field display, the method comprising: sequentially acquiring a user pupil location; digitally computing from at least some said sequentially acquired user pupil location a velocity of said user pupil location over time; digitally comparing said velocity with a designated threshold pupil velocity; digitally rendering the digital image via the light field display in accordance with a maintained light field viewing zone geometry digitally defined in respect of a previously acquired user pupil location unless said velocity is above said designated threshold pupil velocity; and upon said velocity exceeding said designated threshold pupil velocity, digitally adjusting a rendering geometry of the digital image via the light field display so to correspondingly adjust said light field viewing zone geometry to correspond to a newly acquired user pupil location.

In accordance with another aspect, there is provided a computer-readable medium having instructions stored thereon to be automatically implemented by one or more processors to dynamically adjust rendering of a digital image using a light field display by: sequentially acquiring a user pupil location; digitally computing from at least some said sequentially acquired user pupil location a velocity of said user pupil location over time; digitally comparing said velocity with a designated threshold pupil velocity; digitally rendering the digital image via the light field display in accordance with a maintained light field viewing zone geometry digitally defined in respect of a previously acquired user pupil location unless said velocity is above said designated threshold pupil velocity; and upon said velocity exceeding said designated threshold pupil velocity, digitally adjusting a rendering geometry of the digital image via the light field display so to correspondingly adjust said light field viewing zone geometry to correspond to a newly acquired user pupil location.

In accordance with another aspect, there is provided a digital display device operable to automatically adjust a digital image to be rendered thereon, the device comprising: a light field display; a hardware processor; and a pupil tracking engine operable by said hardware processor to automatically receive as input sequential user pupil locations, digitally compute from at least some said sequential user pupil locations a velocity of said user pupil location over time, and digitally compare said velocity with a designated threshold pupil velocity; wherein said hardware processor is operable to digitally render the digital image via the light field display in accordance with a maintained light field viewing zone geometry digitally defined in respect of a previously acquired user pupil location unless said velocity is above said designated threshold pupil velocity, and upon said velocity exceeding said designated threshold pupil velocity, digitally adjust a rendering geometry of the digital image via the light field display so to correspondingly adjust said light field viewing zone geometry to correspond to a newly acquired user pupil location.

One embodiment further comprises digitally adjusting a rendering geometry of the digital image via the light field display so to correspondingly adjust said light field viewing zone geometry to correspond to a function of a newly acquired user pupil location upon a designated condition for movement of said light field viewing zone geometry is met.

In one embodiment, the designated condition for movement of said viewing zone comprises at least one of said user pupil location crossing a defined boundary of said maintained light field viewing zone geometry, said maintained light field viewing zone geometry remaining static for a prescribed period of time, or said velocity is greater than a distinct predetermined threshold.

In one embodiment, the function is an interpolation of said newly acquired user pupil location and said maintained light field viewing zone geometry.

In one embodiment, the function is a function of time since said designated condition for movement was met.

In one embodiment, the interpolation is calculated for a designated period of time after said designated condition was met.

In one embodiment, the designated period of time is between about 0.02 s and 1 s.

In one embodiment, the threshold velocity is between 0.02 m/s and 1 m/s.

In one embodiment, the threshold velocity is approximately 0.1 m/s.

In one embodiment, digitally rendering the digital image via the light field display comprises: digitally mapping the digital image on an adjusted image plane designated to provide the user with a designated image perception adjustment; associating adjusted image pixel data with at least some of said pixels according to said mapping; and rendering said adjusted image pixel data via said pixels thereby rendering a perceptively adjusted version of the digital image.

Other aspects, features and/or advantages will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein:

FIG. 12 is process flow diagram of an illustrative ray-tracing rendering process, in accordance with another embodiment;

Figure 1:
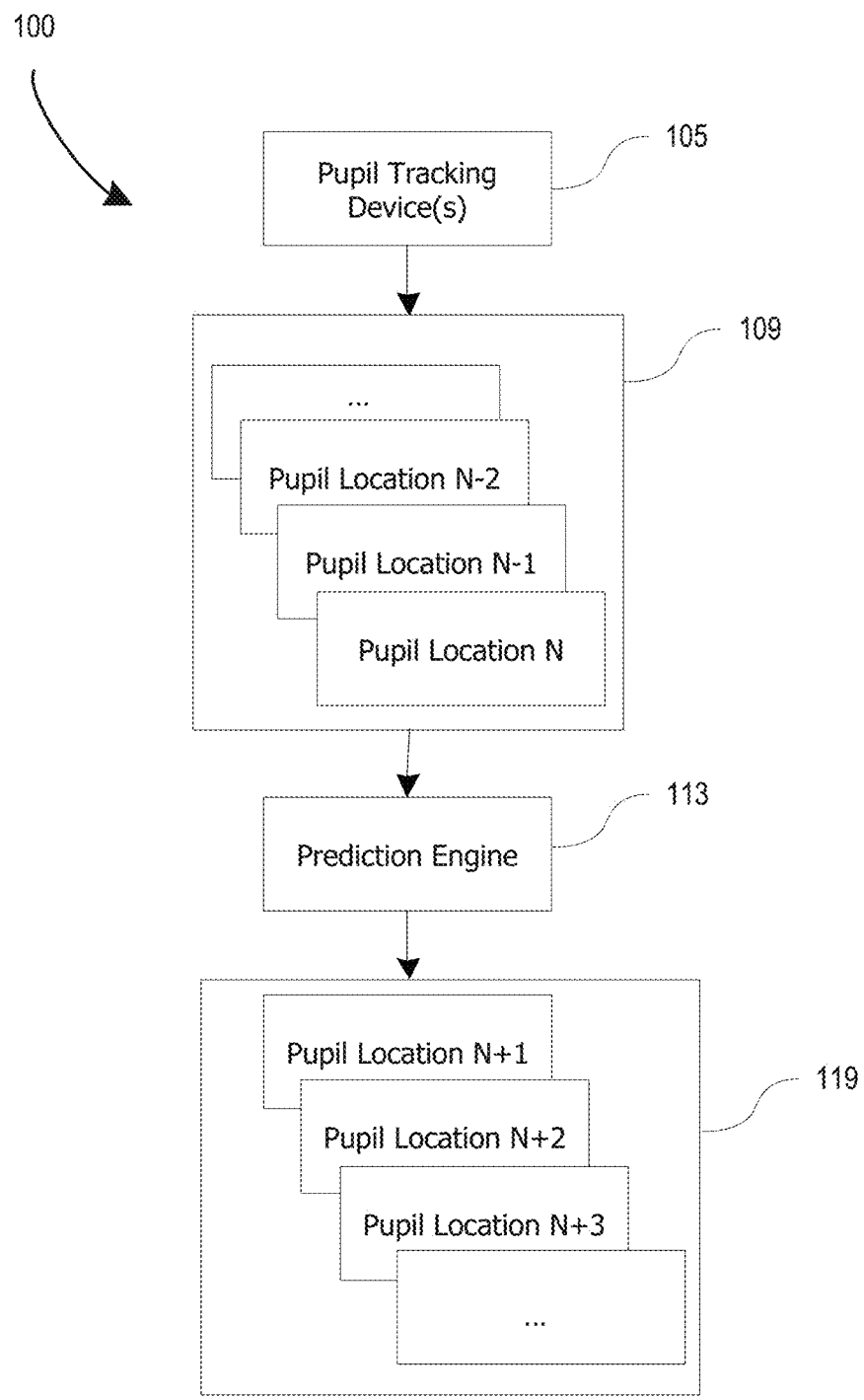
FIG. 1 is a schematic representation of a predicted pupil location calculated using a predictive pupil tracking process based on previously acquired pupil locations, according to one embodiment.

Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood elements that are useful or necessary in commercially feasible embodiments are often not depicted in order to facilitate a less obstructed view of these various embodiments of the present disclosure.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

Various apparatuses and processes will be described below to provide examples of implementations of the systems and methods disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

Unless defined otherwise, all technical and scientific terms used herein have the same meaning as commonly understood by one of ordinary skill in the art to which this invention belongs.

Throughout the specification and claims, the following terms take the meanings explicitly associated herein, unless the context clearly dictates otherwise. The phrase "in one of the embodiments" or "in at least one of the various embodiments" as used herein does not necessarily refer to the same embodiment, though it may. Furthermore, the phrase "in another embodiment" or "in some embodiments" as used herein does not necessarily refer to a different embodiment, although it may. Thus, as described below, various embodiments may be readily combined, without departing from the scope or spirit of the innovations disclosed herein.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or element(s) as appropriate.

The systems and methods described herein provide, in accordance with different embodiments, different examples of a pupil tracking system and method, wherein one or more previously acquired pupil (center) locations can be used to generate and predict one or more future pupil (center) locations, compute an average or current pupil displacement velocity and/or trajectory, or other pupil displacement dynamics as may be relevant to the application at hand. In doing so, in accordance with some embodiments or applications, a corresponding rendering of a perceived image that relies at least in part on pupil tracking inputs, can now take into account not only one or more of a current, past and/or future predicted pupil location and/or gaze direction, but also a past, current and/or future predicted pupil location trajectory and/or velocity, which can ultimately result in providing an increase in the effective rate of pupil tracking (and related image re-rendering), a reduction in re-rendering jitteriness for predictively fixated (and/or pre- and/or post-fixated) pupil dynamics despite ongoing pupil movement capture, and/or other like rendering dynamic improvements. For example, in some such embodiments, a digital display device and digital image rendering system and method are provided that rely, at least in part, on pupil tracking to adjust an output image thereof. For example, an image to be displayed can be adjusted, at least in part, as a function of a tracked user pupil location. In accordance with some of the herein-described embodiments, an output image can therefore be adjusted not only as a function of an available user pupil location, but also or alternatively as a function an acquired and/or predicted user pupil location, trajectory and/or velocity, for example, where an image refresh rate is higher than a pupil tracking rate, and/or to apply a variable rate to image re-rendering and/or to a rendering geometry adjustment mechanism applied to account for pupil displacement (e.g. within a context of a lightfield display or like user-specific directional view generating display devices).

For instance, while existing gaze tracking applications rely on real-time pupil location acquisitions to monitor a user's gaze direction in evaluating what is currently drawing their attention, such gaze tracking systems and methods are typically either insufficiently rapid or precise to support real-time applications requiring high resolution and high accuracy pupil location tracking. For example, the trade-off for operating real-time gaze trackers (e.g. trackers operating on a timescale in the order of roughly 100 ms) is generally a low spatial accuracy, which may nonetheless suffice to monitor a general user gaze direction, whereas higher accuracy solutions will typically be much slower. Accordingly, current solutions are not generally amenable to address applications where both a higher temporal resolution and spatial accuracy may be required, e.g. where current gaze tracking solutions would generate prohibitive lag times and/or adversely impact a user experience. Furthermore, while predictive eye tracking can result in increased tracking and corresponding image rendering rates for improved spatial image rendering geometry accuracy, predictive eye tracking techniques as described herein may also allow for such high precision, high accuracy pupil-specific image rendering processes to accommodate different view modes, for example, to dynamically adjust pupil displacement impacts on image rendering based on acquired and predicted pupil dynamics, e.g. as a viewer alternates between moving and fixated view periods, as will be described in greater detail below.

For example, in accordance with some of the embodiments herein described, pupil location tracking and/or prediction may play an important role in light field display systems, wherein a rendered image(s) provides an optimal viewing experience in a defined region(s) of viewing space, herein referred to as a view zone, or viewing zone. In such embodiments, applying predictive techniques based on acquired pupil locations and derived pupil velocity/trajectory considerations can result in a significantly improved viewer experience whereby a relatively fixated gaze can be recognized by virtue of reduced pupil velocities or likewise recognizable fixated pupil location dynamics (e.g. constrained trajectory, limited displacement amplitudes, recognizable behavioural pupil dynamics for a particular activity such as reading, etc.), thus invoking a "fixated" (and/or pre- and/or post-fixated) viewing mode or state in which an image rendering geometry is not as often updated for pupil location, thus significantly reducing potentially perceived image jitteriness and/or stability. Comparatively, where captured pupil locations are suggestive of significant pupil displacements, the pupil tracking system and correlated image rendering process can migrate to a "moving" mode whereby image rendering dynamics and geometries are more rapidly updated to accommodate such movement.

For example, in some of the herein-described embodiments, a pupil tracking system and method is implemented for the purposes of applying adaptive image corrections or adjustments in a light field display system or device, whereby acquisition of a temporally and spatially accurate pupil location, in three-dimensions, is important in the delivery of a positive user experience. For example, certain embodiments involve the provision of corrective image rendering through light field shaping optics so to correct for a user's reduced visual acuity. An exemplary application for the herein-described embodiments is described in Applicant's U.S. Pat. No. 10,394,322, Applicant's co-pending U.S. patent application Ser. Nos. 16/510,673, 16/569,137, and 16/551,572, the entire contents of each of which are hereby incorporated herein by reference. An example drawn therefrom is also described below, in accordance with one embodiment. In such embodiments, high pupil location accuracy may be appreciated to ensure desired image corrections are adequately generated while minimizing the production of optical artefacts that may otherwise be distracting to the viewer. Given the high spatial resolution considered to implement such corrections, a high temporal sensitivity can also be addressed as slight displacements in the viewer's pupils may bring forth significant changes in ray tracing, or like vision correction computations, applied to compute the various optical views provided through the light-field display and its impact on image correction and focused image rendering. As the viewer's eyes can readily perceive fluctuations within a temporal range of a few dozen milliseconds, a temporal pupil tracking resolution may be required in this order, in some embodiments, to ensure a quality user experience. Namely, pupil tracking outputs may be preferred on timescales similar to, or in the order of, an image refresh rate, so to ensure that appropriate image rendering is provided to provide the desired visual compensation without introducing adverse visual effects or delays. Conversely, and in accordance with some embodiments, where pupil displacements are tracked and/or predicted to remain within a relatively confined viewing zone, for example as prescribed or bounded by display hardware, optics and/or viewer positioning, a rendering geometry of the lightfield display may be maintained so not to overly refresh, for example, ray tracing and/or view zone pixel allocations, thereby reducing or minimizing perceived image rendering jitteriness that could otherwise be perceived due to an oversensitive pupil tracking and image rendering system. Indeed, a viewer identifiable as being within a fixated or static view configuration (i.e. where pupil displacements are predictively contained within or reasonably around a designated view zone, eye box, etc.), may ultimately have a better viewing experience if image rendering dynamics/geometries are not as frequently updated, for instance, favouring image rendering stability over spatial accuracy. A highly spatially and temporally sensitive system may nonetheless be preferred where the viewer's fixated mode migrates to a moving mode, in which pupil tracking and rendering accuracy and precision may be of greater importance to an effective viewer experience.

Given the temporal constraints and considerations noted above, predictive pupil tracking can be implemented, in accordance with some of the herein-described embodiments, so to mitigate delayed optical effects that may impact a viewer's experience and consequently provide for a better overall user experience, while also or alternatively mitigating jittery optical/image rendering effects that may be perceived when a viewer is otherwise mostly in a static or fixated viewing state.

The following will provide different examples of pupil tracking and correlated image rendering techniques that rely on acquired and/or predicted pupil locations, velocities and/or trajectories to improve a user experience, as introduced above.

With reference to FIG. 1, and in accordance with one exemplary embodiment, a predictive pupil tracking system, generally referred to using the numeral 100, will now be described. In the illustrated embodiment of FIG. 1, the system 100 relies on one or more pupil tracking devices or systems 105 to output a current pupil location. These may include, without limitation, any system using corneo-scleral reflections (i.e. glints) on the user's eye, from one or more IR or near-IR light sources or the like (for either bright and/or dark pupil tracking); or computer vision-based methods using feature recognition applied to an image of the user's face obtained via a digital camera of the like.

Note that different devices using different technologies may be used in combination, for example, to leverage computation efficiencies in tracking and/or monitoring a user's eye and/or pupil location in different environments, and/or to provide metrics by which system accuracies can be evaluated, and different approaches weighted accordingly to provide higher overall system accuracies. Furthermore, different techniques may be implemented, for example, to reduce overall system power consumption, computational load, reduce hardware load requirements and/or reduce the viewer's exposure to various light probes (e.g. IR, Near-IR probes) typically used in glint-based pupil locating processes. For example, machine vision implementations may be relied upon at a first level to adequately locate and track facial features such as the user's eyes, pupils and pupil centers, whereas higher-resolution glint-based techniques may be layered thereon (e.g. via IR/NIR illumination) to refine and/or confirm machine vision results at a lower frequency, thus reducing IR/NIR emissions which may be unfavourable in certain conditions but may otherwise be required in other low lighting conditions. Similarly, different spatial estimation techniques may be applied to, again, reduce computational load by, for example, estimating pupil center locations using machine vision techniques by predominantly tracking eye locations (which are easier to track in general) and confirming pupil locations and/or centers at lower refresh rates. These and other techniques may be considered herein without departing from the general scope and nature of the present disclosure.

With continued reference to FIG. 1, generally, device(s) 105 is(are) operable to provide a sequence of pupil center positional data 109 of a user (e.g. 3D position of the pupil center) in real-time or near real-time. For instance, where different techniques are used to computed pupil center locations 109, these different outputs may be combined, averaged and/or otherwise statistically compiled to produce pupil center location information useable in subsequent steps. For example, in some embodiments, a machine-vision based approach may be used to first estimate a location of the pupils. This estimation may rely on various facial feature identification and/or extraction techniques, for example, but not limited to, by searching for and/or identifying the curvature of the eye(s), the dark pupil centers in contract with the sclera, etc., in combination, for example, with one or more glint-based techniques that, for example, may be constrained to previously machine-identified eye/pupil regions and/or be used a confirmation, validation or recalibration of such techniques. In some examples, past pupil locations may not only be used, directly or indirectly through one or more encoded variations or transformations thereof, to output predictive pupil location information, but also to seed pupil location measurements, for example, in the context of a machine vision pupil search algorithm or the like.

With continued reference to FIG. 1, the system 100 uses, at least in part, data 109 as an input to a Prediction Engine 113 configured to analyze and generate therefrom one or more temporally predictive pupil locations 119 based on characteristic patterns automatically derived and interpreted from input data 109. For instance, one or more predictive data modeling techniques may be used by Prediction Engine 113 to extract one or more parameters representative of monitored real-time pupil location variation, and generate or construct therefrom a mathematical representation or model operable to output predictive pupil locations 119. Some of these techniques will be discussed below, without limitation.

In some embodiments, one or more temporally predictive modeling methods (statistical or otherwise) can be used by Prediction Engine 113 to generate a predictive pupil location sequence 119. These may include, but are not limited to: moving averages, exponential smoothing, linear and/or non-linear regressions, spline interpolation, Box-Jenkins forecasting methods, Kalman Filters, alpha-beta filters, non-parametric models such as Gaussian Process Models and/or neural networks (including convolutional, recurrent or recursive neural networks). Other filters may also or alternatively include a weighted median filter, or the like. Generally, any amount of previously generated pupil location data, and/or data derived therefrom (e.g. velocity, acceleration, displacement trends or patterns, etc.) may be used in the estimation or extrapolation of the pupil center location to produce predictably reliable results. In some cases, a trajectory model (e.g. probable pupil location as a function time) from past data points may be extrapolated or projected beyond the last data point (pupil center location) to obtain an estimated trajectory (as a function of time) of (probable) future pupil locations. Moreover, any number of estimated locations may be generated from the estimated trajectory while waiting for the next true pupil center location measurement, which can then be relied upon to refine the estimated trajectory and iteratively apply appropriate correction thereto to output ongoing predictive pupil location data. As noted above, while a predicted future pupil location may be used to predictively induce a corresponding image rendering process (e.g. to predictively output an appropriate image rendering geometry and/or perspective), acquired pupil tracking data may also or otherwise be used to compute a current or predicted pupil trajectory, and/or again consider a current or average pupil velocity, so to effectively predict the likelihood that the viewer's pupil will sufficiently move within a forecasted time period to warrant impacting/adjusting current image rendering parameters.

In some embodiments, each pupil center location obtained from the pupil tracking device or system 105 may also comprise measurement errors associated therewith. These errors, if present, may be used by Prediction Engine 113 when generating the estimated pupil center sequence 113. The methods for incorporating such measurement errors in the modelling methods described above are well known in the art.

Figure 2:
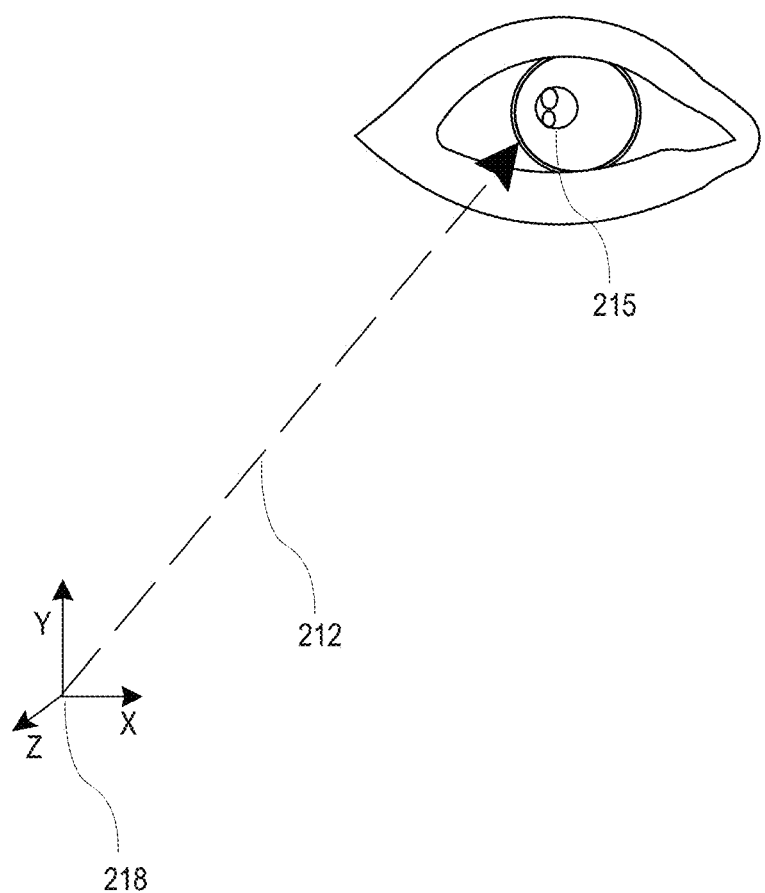
FIG. 2 is schematic representation of a pupil location in three-dimensional space, according to one embodiment.

As shown in FIG. 2, and in accordance with one embodiment, a pupil location is the three-dimensional position 212 of the pupil center 215 measured from a reference point 218. While the pupil moves slightly within the eye depending on where a user is focusing his/her gaze, the head and body of the user itself may move as well. Within the context of a vision correction application, or other 3D light field image perception adjustment applications, the pupil location in three dimensional space is generally set relative to a location of a light field display screen such that, in some embodiments, appropriate ray tracing processes can be implemented to at least partially govern how light emanated from each display pixel (of interest) is appropriately channeled through a corresponding light field shaping layer and relayed to the viewer's pupil. Naturally, as a viewer's pupil location changes relative to the display, so will corrective or otherwise adjusted pixel data change to adjust the output pixelated image accordingly. Accordingly, the light field display will generally include, or be associated with, related pupil tracking hardware such as one or more light sources (e.g. IR/NIR) and/or cameras (visible, IR, NIR) and related pupil tracking firmware/software. Further details in respect of one illustrative embodiment will be described below.

Figure 3:
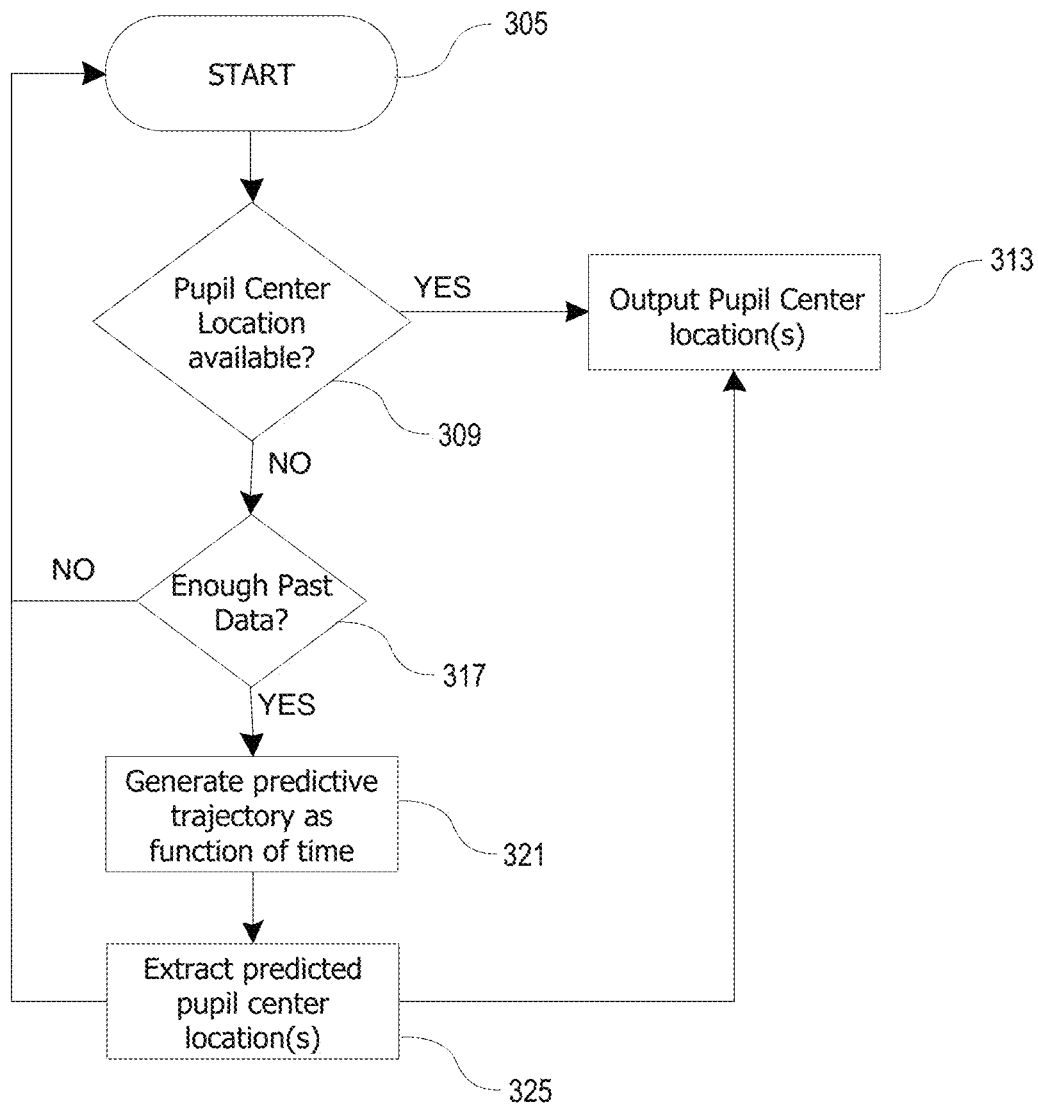
FIG. 3 is a process flow diagram of a predictive pupil tracking method, according to one embodiment.

With reference now to FIG. 3, and in accordance with one exemplary embodiment, a predictive pupil tracking method using system 100 described above, and generally referred to using the numeral 300, will now be described. The above-described system 100 uses a sequence of pupil locations to generate predictive estimations of future pupil locations. As noted above, it will be appreciated that other direct, derived or transformed pupil location data may be used to this end. For simplicity, the following examples will focus on predictive trajectory models based on a time-ordered series of previously stored pupil locations.

The system described may thus be leveraged to complement or improve these pupil-tracking systems by generating one or more future pupil locations while another system or device is waiting for the eye or pupil tracking systems to acquire/compute a new location. Thus, the method described herein may provide for an improved frequency at which pupil locations are provided as output to another system or method. For instance, output of a current pupil location may be delayed due to processing load and/or lag times, resulting in the output, in some applications, of somewhat stale data that, for example, when processed within the context of highly sensitive light field rendering applications (that will invariably introduce their own computational lag), result in the provision of a reduced viewer experience. Conversely, viewer experience may also or otherwise be adversely affected if pupil-tracking systems perceive a user pupil to have shifted, for instance through digitization of user pupil positions, error in pupil location measurements, or minor spurious pupil movements from an otherwise stationary user. Such a phenomenon may result in a re-rendering of an image or adjustment of an image rendering geometry, in a situation where user experience may be improved, for instance, by not adjusting pixel data at all. Namely, an image rendered with the intent of providing a designated image perception for a given input pupil location may be unsatisfactorily rendered for the viewer if the viewer's pupil location changed significantly, or erroneously perceived to have changed, while image rendering computations were being implemented. Accordingly, computational lag times, combined with the generally high refresh rates required to provide an enjoyable viewer experience, may introduce undesirable effects given at times noticeable pupil location changes, or a light field display refreshes unnecessarily due to inaccurate instantaneous perception of movement. Using predictive pupil location data in light field rendering applications, as considered herein, may thus mitigate issues common with the use of otherwise misleading pupil location data.

Accordingly, the systems and methods described herein may be used to advantage in light field rendering methods or systems in which the pupil center position of a user is used to generate a light field image via a light field capable display or the like. Indeed, the predictive pupil tracking method described herein, according to some embodiments, may make use of past pupil positional data to improve the speed or frequency at which the pupil center position, which may be a moving target, is available to a light field ray tracing algorithm, or like light field rendering process. Since the light field rendering embodiments described above rely, in part, on having an accurate pupil center location, the speed or frequency at which the pupil positional information is extracted by the pupil tracker may become a bottleneck for the light field rendering algorithm. A 60 Hz digital display (most phone displays, for example) will have a refresh rate of about 15 ms, whereas higher frequency displays (e.g. 120 Hz displays) have much faster refresh rates, which imposes significant constraints on the computation and output of accurate pupil tracking data, particularly when combined with computation loads involved in most light field rendering applications. For instance, for an optimal light field output experience, a rendered light field should be refreshed at or around the display screen's refresh rate. This refresh rate should naturally align with a current location of the user's pupil at that time and thus, benefits from a predictive pupil tracking approach that can extrapolate, from current data, where the pupil will actually be when the screen next refreshes to render a new light field output. Otherwise, the lack of temporal accuracy may lead to a reduced visual experience. Conversely, the importance of a high refresh rate for many applications in which a user is moving may unduly prioritise computational resources for image refreshing when a user is substantially stationary, or pupils are moving at low velocity, which, for at least the abovementioned reasons, can also adversely affect user experience. Available computational power may thus be leveraged instead to predict or estimate, based on previous known (e.g. measured) pupil center locations, an estimated future location of the pupil center and selectively use this estimation to update the light field image, as appropriate, while waiting for the next true pupil center location measurement, thereby resulting in a smoother viewing experience.

Coming back to FIG. 3, a pupil location iterative refresh cycle is started at step 305. The method first checks at step 309 if, at this time, an actual measured pupil location is available from the one or more pupil tracking device or system 105. If this is the case, the method outputs the measured pupil location at step 313. If this is not the case, then at step 317, the method checks to see if enough prior pupil center locations (as measured by one or more pupil tracking device or system 105) have been recorded to provide enough data for prediction engine 113 to provide an accurate predicted one or more future pupil locations. If this is not the case, then the method goes back to step 305. If enough data is available, then the method uses, at step 321, Prediction Engine 113 to generate the most probable trajectory (position as a function of time) of future pupil locations. It may then, at step 325, extract one or more future pupil locations from this trajectory, which are then fed back as output (step 313). The method loops back to step 305 once more. Therefore, the method as described above, may ensure that measured pupil locations are outputted and used as soon as possible, while relying on Prediction Engine 113 to generate data points in between.

Similarly, predictive pupil tracking data can be used to accommodate predefined light field rendering lags, for example, where a pupil location is required early on in light field rendering computations (e.g. ray tracing) to output corrective or adaptive pixel data for rendering. Accordingly, rather than to compute ray traces, for example, on the basis of a current pupil location output, such computations may rely on a predictive location so that, when the corrected or adjusted image is finally computed and ready for display, the user's pupil is most likely now located at the predicted location and thus in an ideal location to best view the rendered image. A predictive location may also be identified as one in which the image currently being displayed requires no further adjustment (i.e. the user's pupil is most likely already located in or around an ideal location to best view the rendered image), for example if the user pupil is stationary or moving slowly. In such a situation, light field rendering computations may be bypassed altogether for a time in favour of saving computational resources or improving user experience. These and other time lapse, lags and synchronization considerations may readily apply in different embodiments, as will be readily appreciated by the skilled artisan.

Figure 4:
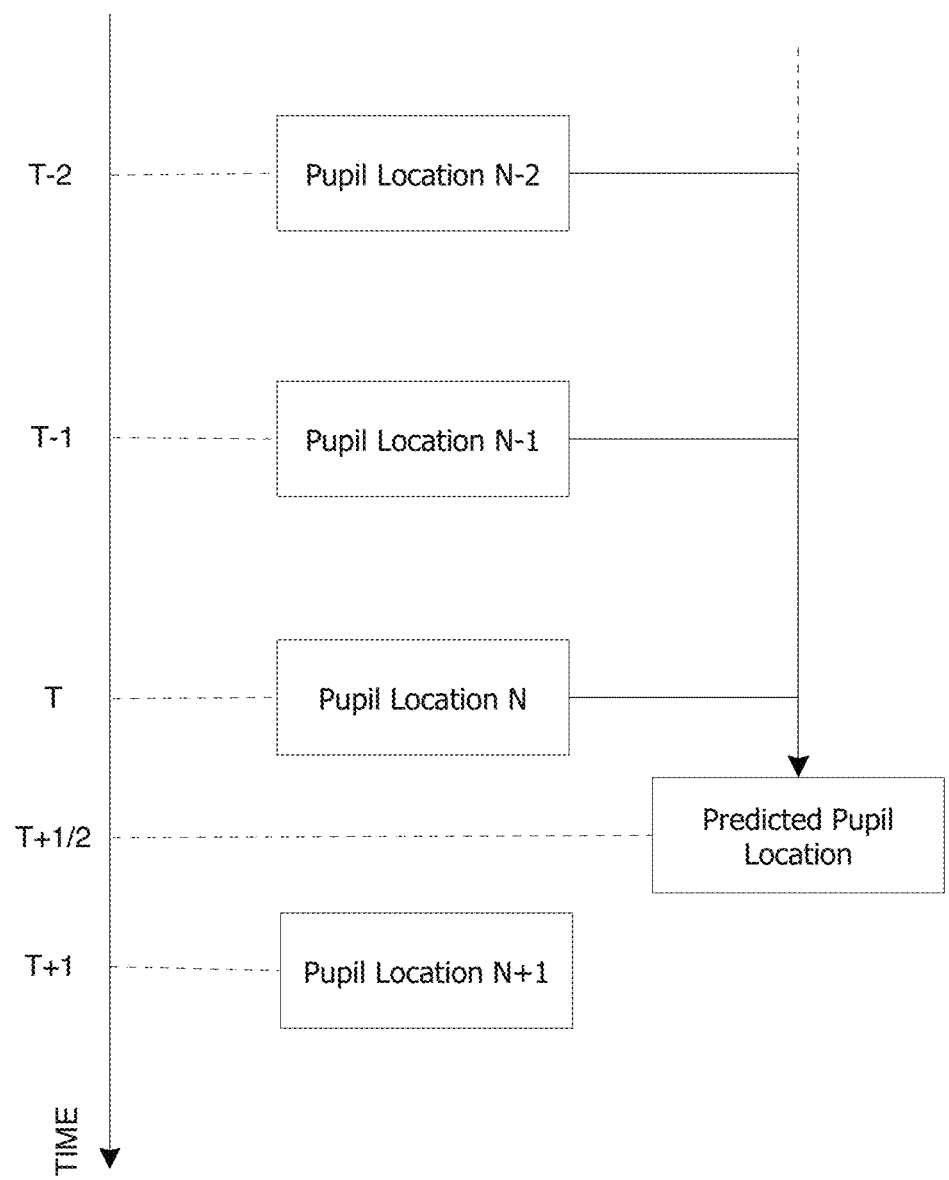
FIG. 4 is a schematic representation of an effective pupil tracking frequency increased using a predictive pupil tracking process such as that sown in FIG. 3, according to one embodiment.

FIG. 4 shows an exemplary schematic diagram relating a consecutive sequence of pupil location measurements with a corresponding time sequence (by a single unit of time for simplicity). Hence, the sequence from N to N+1 implies a time difference of one unit. Therefore, by using past pupil locations (N, N−1, N−2, etc.) to generate a most probable future pupil location at time T+½ (for example), the frequency at which pupil locations are available is effectively increased by a factor of two. Likewise, a predictable pupil location may be forecasted when addressing higher computation load processes.

Figure 5A:
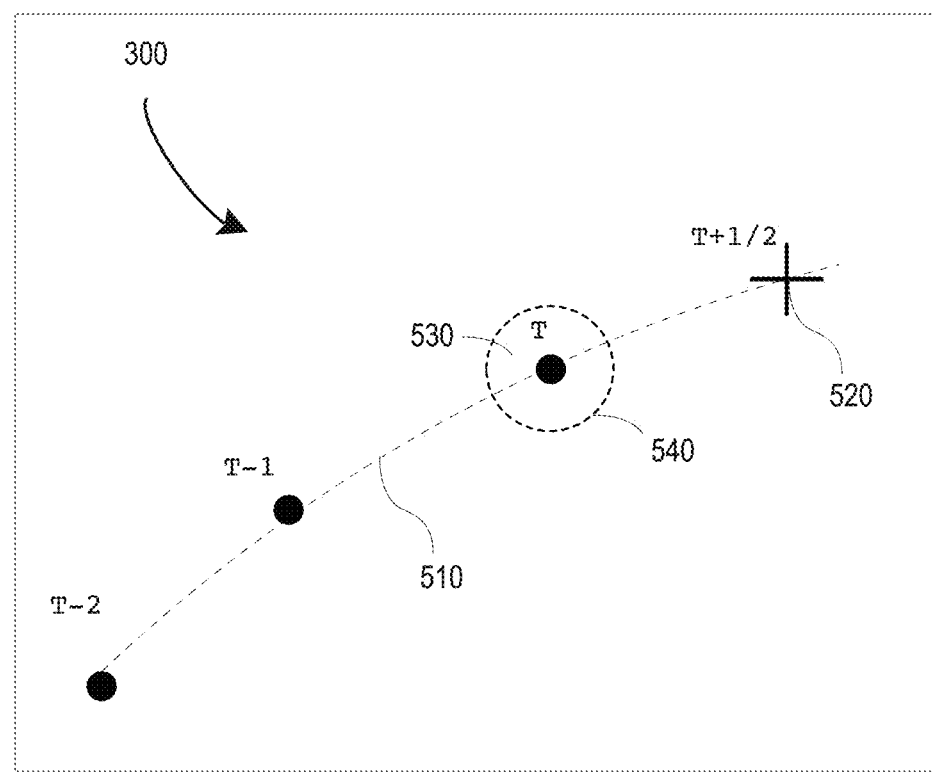
FIGS. 5A and 5B are schematic representations of acquired pupil location sequences and forecast pupil locations predicted therefrom, in accordance with at least one embodiment.

FIG. 5A shows the positional change corresponding to the time sequence illustrated in FIG. 4. The skilled technician will understand that the use of a 2D representation is only for demonstration purposes and that an additional depth component can also normally be used. As explained above, each point (T−2, T−1 and T) represents a sequence of measured pupil center locations, separated in time. At time T, while waiting for the next measurement (the result of which will be available at time T+1), previous measurements (N, N−1, and N−2 from times T, T−1 and T−2 in this example) may be used to generate an estimated trajectory 510 of probable future pupil center location and extract therefrom an estimated future pupil location 520 at time T+½.

As will be appreciated by the skilled artisan, gaze or pupil tracking comprises an important element of many light field display systems, such as those comprising an array of light field shaping elements (e.g. microlens arrays, apertures, and the like), which may produce the highest quality images within a specific region(s) of space, or a view zone. User experience may therefore be improved when an image is rendered taking into account a user pupil location or predicted location. Referencing again FIG. 5A, a light field image rendered at time T may therefore be optimally viewed within a view zone 530. A view zone geometry may be defined by the light field display components and/or light field shaping element sizes and/or geometries. One skilled in the art will therefore readily appreciate that while the view zone 530 is represented with a boundary 540 that is represented as circular in FIG. 5A, such a boundary may be hexagonal, rectangular, stretched hexagonal, etc., and is not limited to two dimensions. In this example, if the pupil location at time T is utilized to render an image for a moving viewer, who will then view the image at the pupil location at time T+½, the viewer may not receive a high quality image at time T+½, as the pupil location may then lie outside of the view zone for which the image was optimally rendered. However, by estimating the trajectory 510 of the user's pupil over time, a prediction engine, such as that described above as element 113 of FIG. 1, may, in accordance with at least one embodiment, estimate pupil location coordinates at time T+½ in order to project an image corresponding to a view zone that may encompass the predicted pupil location 520, thereby providing a more positive viewing experience.

Figure 5B:
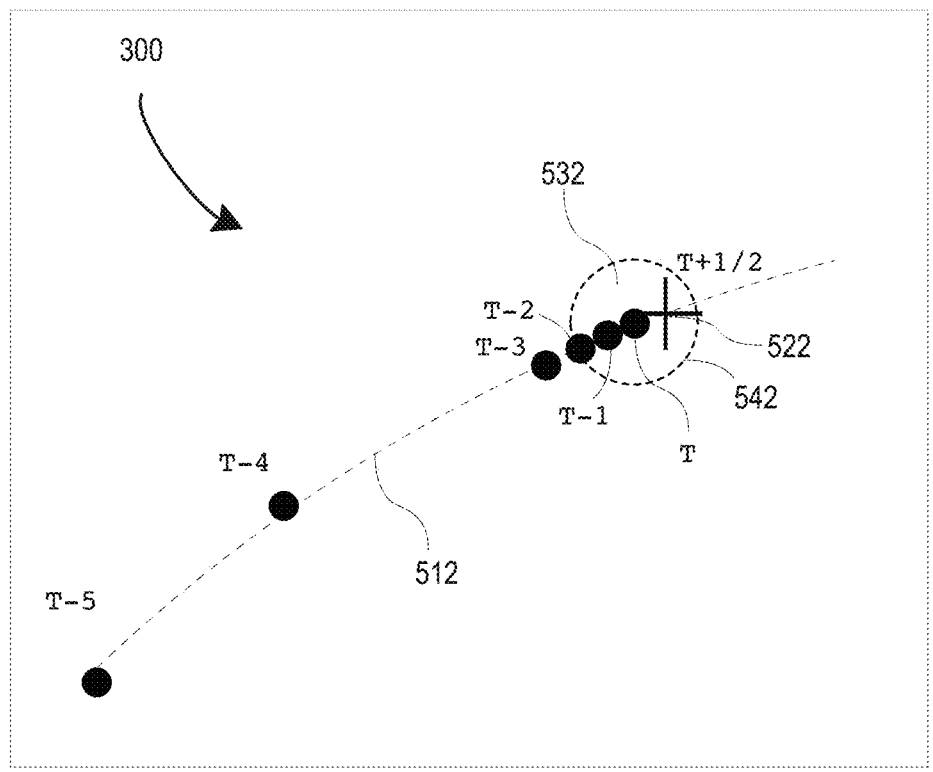

Similarly, FIG. 5B highlights yet another embodiment in which a prediction engine 113 may improve viewer experience. In this example, a user pupil location follows an initial trajectory similar to that shown in FIG. 5A, as denoted by the pupil locations, in order, T−5, T−4, and T−3. However, in this example, in contrast to that of FIG. 5A, a user pupil slows in its movement after T−3. In this example, the user pupil may be measured as having a trajectory and/or velocity small enough that its position 522 at time T+½ may still lie within a boundary 542 of the view zone 532 produced at time T. In this case, and in accordance with at least one embodiment, adjusting an image rendering geometry (e.g. geometrically re-allocating pixel values based on a distinctly computed optimal view zone) so re-render a digital image (e.g. for a static image) or impact rendering of future time-sequenced images (e.g. for a dynamic image) may not correspond to an improvement of user experience, but may even be detrimental thereto. For at least the reasons discussed above, it may be beneficial to therefore not refresh and/or re-render a display geometry in favour of providing a stable image geometry if a prediction engine 113 predicts a pupil location 522 that will not significantly deviate in space from previous recorded locations.

Figure 6:
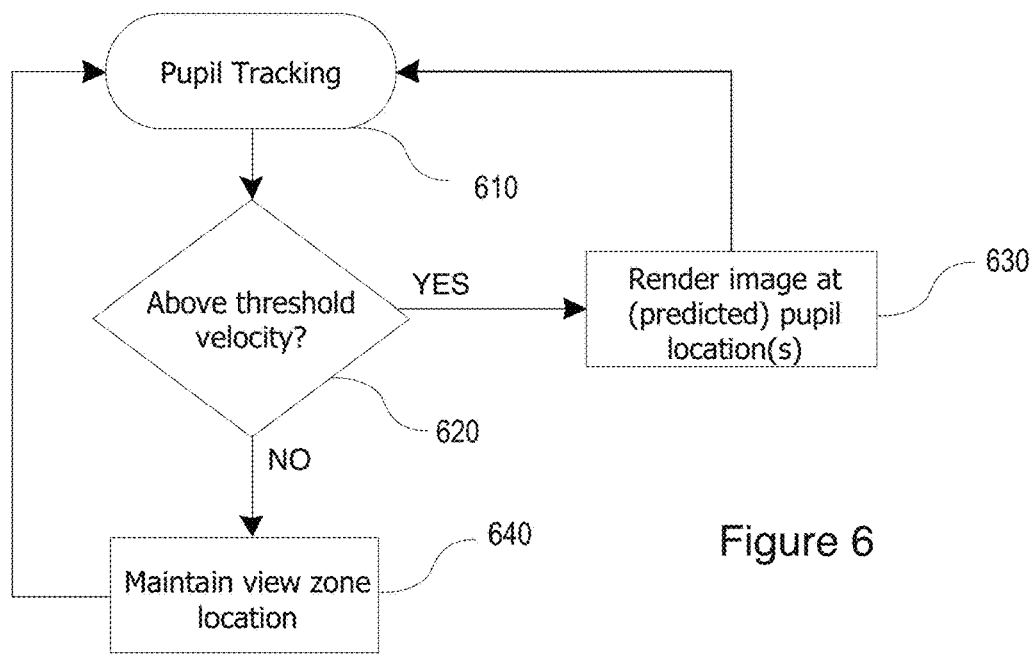
FIG. 6 is a process flow diagram illustrating an operational mode of a predictive pupil tracking method, in accordance with at least one of the various embodiments.

Accordingly, a prediction engine such as that depicted in FIG. 1 as herein described may utilise a number of pupil positions and/or velocity data, or calculated values related thereto, to improve user experience. In accordance with at least one embodiment, it may be sufficient to measure or calculate a user pupil velocity in order to predict that an image re-rendering may be unnecessary, if, for instance, a predicted pupil location is within an existing view zone. Such a prediction may be performed using said velocity, as well as optionally one or more of a view zone geometry, an image rendering rate, lag time, computational requirement, or the like. To simplify computation, and in accordance with at least one embodiment, a user pupil threshold velocity may be provided as an input parameter such that view zone re-optimization may be paused when it is determined that a pupil is moving with a relatively low velocity. FIG. 6 shows a schematic example of a predictive pupil location process that may be employed to provide an image within a viewing zone for a user that is perceived as stable, in accordance with at least one embodiment. In this example, a pupil tracker obtains a user pupil location and/or motion at step 610, which may then be used to derive a pupil velocity. A processor and/or predictive engine may use this velocity to predict whether a pupil is moving sufficiently fast to warrant computing a new viewing window/zone location within which to render an image, and then perform further computations related to, for instance, ray tracing. The predictive engine may, in accordance with some of the various embodiments, compare the measured velocity to a designated threshold velocity at step 620. If the measured velocity is above the designated threshold, it may be deemed sufficiently high to render an image to be projected within a new view zone. In this case, the location of the new view zone and corresponding image(s) may be chosen to be at the location of the pupil at the time of the position and/or velocity measurement, or a predicted location based on a predicted trajectory, as described above. If the velocity is less than the designated threshold, it may be predicted that at a future time, a pupil's location may still reside inside or sufficiently around the present view zone, in which case user experience could benefit from maintaining the current location of the view zone and corresponding image(s) at step 640 without re-rendering and/or performing potentially demanding computations. The skilled artisan will appreciate that pupil tracking 610 may also be performed at higher rates than the decision-making and rendering steps of FIG. 6.

Threshold values, in accordance with various embodiments, may be chosen on a variety of bases, non-limiting examples of which are view zone sizes or geometries, typical pupil speeds for a particular display system, display system properties, specific applications for which a display is typically used, or the like. For instance, if a view zone geometry and size, and a display rendering rate are known for a given pupil location, a processor may determine the speed at which a pupil would need to move in order to predict that the pupil will have left the view zone by the time a subsequent rendering could be performed. Such velocity thresholds may also be adaptive or predictive in nature, or may be adjustable, for instance, via a setting on the display to be programmed or tuned by a user. A threshold may also be set based on an empirical determination of user experience for a specific device, application, or setting, in accordance with yet another embodiment. For some embodiments, a threshold value is set to be on the order of 0.1 m/s.

Figure 7:
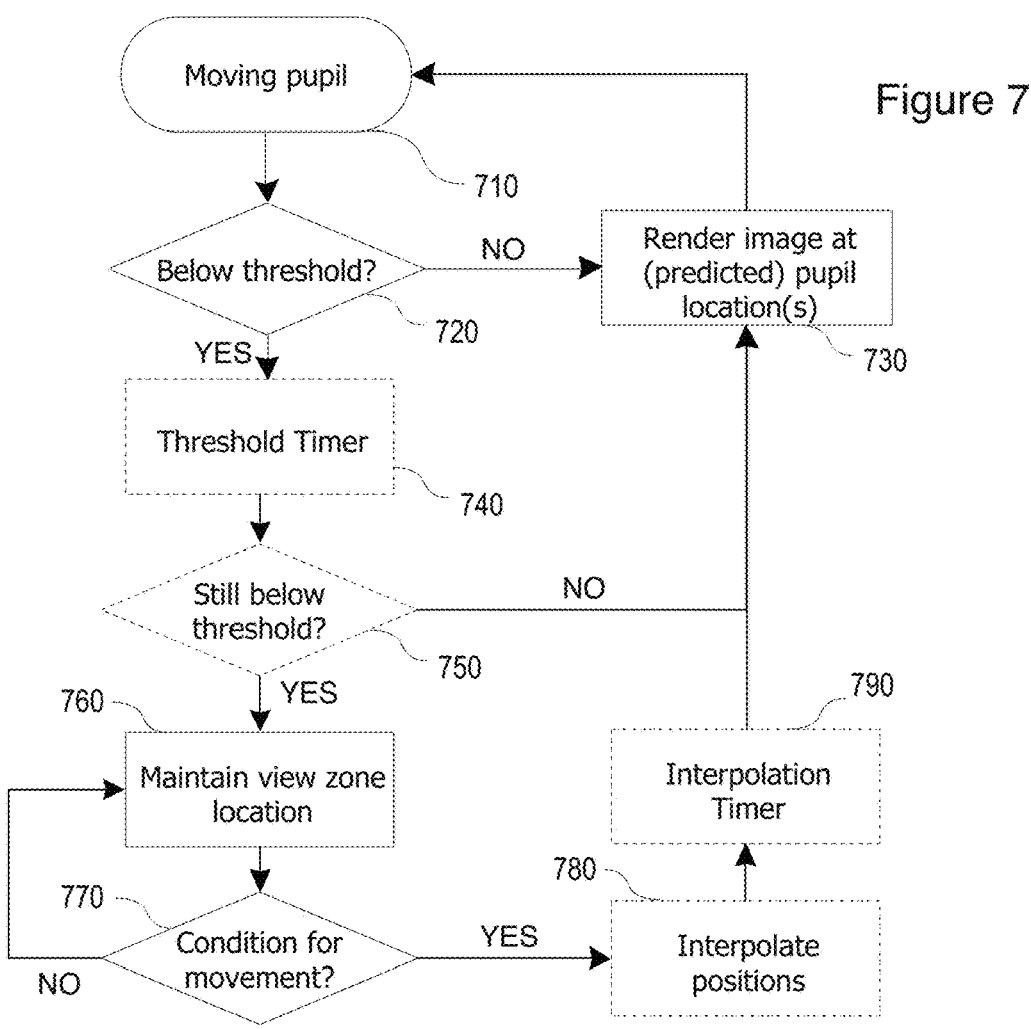
FIG. 7 is a process flow diagram illustrating another operational mode of a predictive pupil tracking method, in accordance with at least one of the various embodiments.
Figure 14:
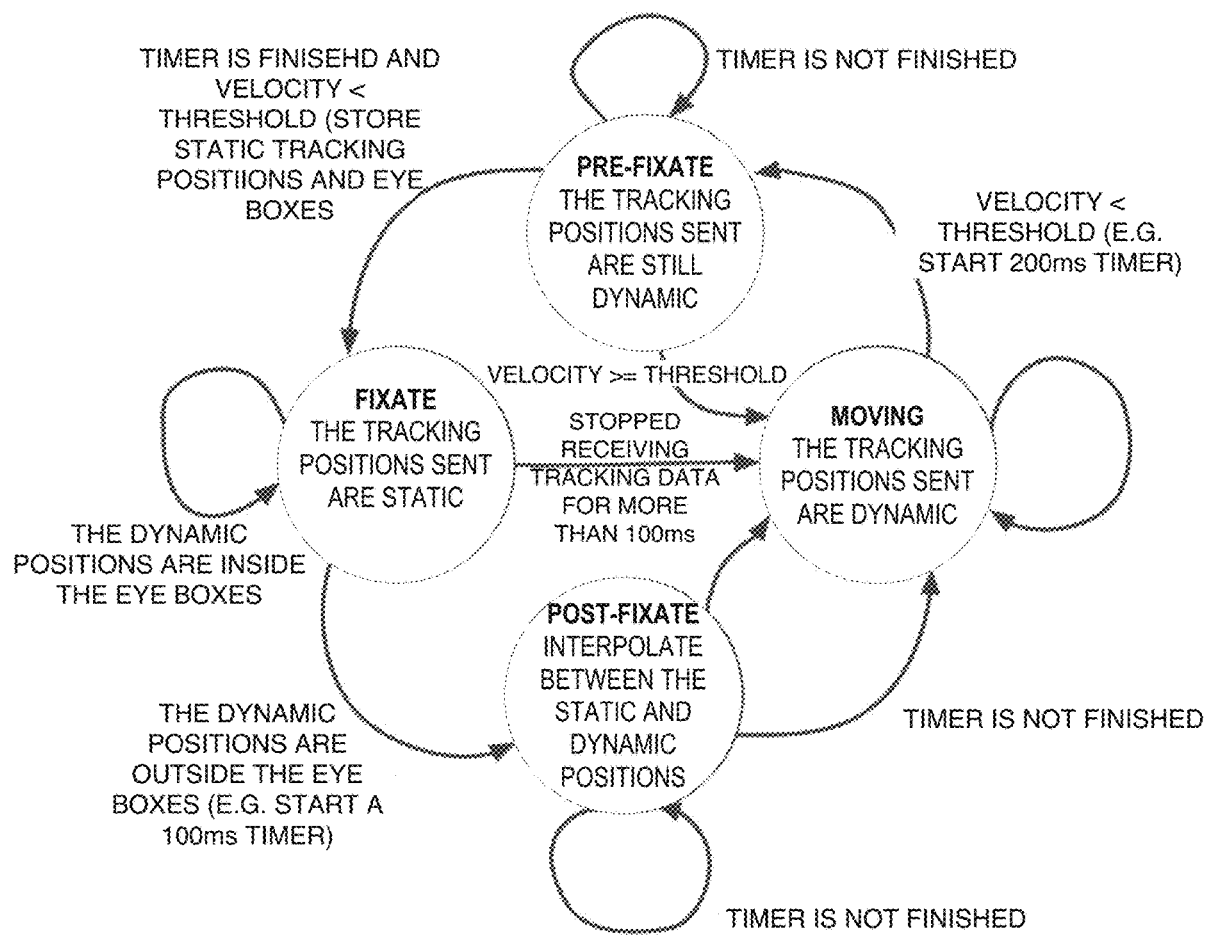
FIG. 14 is a schematic state diagram of a predictive pupil tracking system, in accordance with one embodiment.

FIG. 7 shows a schematic diagram of an exemplary process for an improved user experience via predictive pupil determination, in accordance with another embodiment. Reference is also made to FIG. 14 in which different exemplary viewer pupil dynamic states, and transitions therebetween, are also illustrated. In this example, a pupil tracker obtains position and/or velocity data related to a pupil or pupils. If the determined pupil velocity is not below a certain threshold (i.e. the pupil is determined to be in a "moving" mode), as determined at step 720, images will be rendered to be projected within a view zone in a new location in step 730, wherein the new location may correspond to either the latest pupil location as determined by the pupil tracker, or at a location predicted from related pupil location data to provide a positive viewer experience. If the pupil velocity is below the designated threshold (i.e. the pupil is in a "fixate" mode), it may be determined that the current view zone location may be acceptable for a pupil at a subsequent time, in which case the current view zone location may be maintained at step 760.

In accordance with some embodiments, various criteria may be additionally applied to maintain the view zone location. For example, it may be required that the measured or calculated pupil velocity be below the velocity threshold for a certain amount of time (e.g. 200 ms) as measured using a digital timer 740 (i.e. the pupil is "pre-fixate"). An exemplary process may then repeat the comparison of the velocity to the threshold at step 750, either repeatedly throughout a designated threshold wait period, or again at a specific later time. Other criteria or methods to filter or otherwise provide a reliable decision on movement may be employed without departing from the general scope of this disclosure. If the condition of being below the threshold is not met at step 750, the view zone location and corresponding image(s) may then be rendered for projection at a new location in step 730. Otherwise, the current view zone location may be maintained at 760.

A view zone location may be maintained for an amount of time that is deemed appropriate, or until one or more conditions for determining movement 770 are met. In accordance with various embodiments, non-limiting examples of a condition for movement may be that a tracked pupil location has been determined to have crossed a boundary of the current view zone, that a second threshold velocity, which may or may not be the same threshold velocity used to initiate maintaining of a view zone location, has been observed for the pupil, that pupil tracking data is no longer available or has not been received for a designated amount of time (e.g. a processor or application has stopped receiving tracking data for more than, for instance, 100 ms), or that a timer has expired (e.g. a view zone has been static for, for instance, 100 ms).

Optionally, and in accordance with various embodiments, another step or steps may be employed to improve a viewer experience before returning to rendering at a current or predicted pupil location at step 730. A non-limiting example may be that, given that the pupil was recently below a designated threshold velocity, the pupil may be predicted to benefit from a view zone that is in a similar location to the previous view zone, even though a condition for movement has been met (i.e. the pupil considered to be in a "post-fixate" mode). For instance, if the pupils are determined to have crossed a boundary of the view zone in step 770, their velocity may still be low, and a new view zone location that would provide a positive viewing experience would lie somewhere between the new pupil location and the previous location. This new view zone location may therefore be an interpolation, as in step 780, of the previous view zone location and the pupil location. Non-limiting examples of an interpolation as herein described may be an average, a weighted average, or some other function for which a positive viewing experience can be predicted. The interpolation may be performed for a designated amount of time 790 after a condition for movement is met, or may, alternatively or in addition, be a function of time since the condition was met. For instance, if a condition for movement has been met due to a pupil location crossing a boundary of a static view zone, the next rendered view zone location may be a weighted average between the previous view zone location and the current pupil location, wherein every 10 ms, the weight of the pupil location in the weighted average increases in increments of 10%, until, after 100 ms, the location of the view zone will be that of the tracked pupil, as in step 730.

The skilled artisan will appreciate that interpolation steps may be optionally implemented based on the means by which a condition for movement was met. For instance, if a pupil location has been determined to have crossed a boundary of a static view zone, and/or is deemed to be moving below a certain speed, an interpolation of pupil position and previous view zone location may be performed over 100 ms to calculate the next view zone location. However, if a system implementing a process herein described stopped receiving tracking data for 100 ms, view zone location may be updated based solely on new pupil location data, as in step 730, in accordance with at least one embodiment.

EXAMPLE

The following example applies the predictive pupil tracking systems and methods described above within the context of an adjusted pixel rendering method used to produce an adjusted user image perception, for example, when applied to a light field display device. In some embodiments, the adjusted user image perception can accommodate, to some degree, a user's reduced visual acuity. To improve performance and accuracy, the user's pupil location, and changes therein, can be used as input, either via an integrated pupil tracking device and/or engine, or via interface with an external device and/or engine.

For instance, the devices, displays and methods described below may allow a user's perception of an input image to be displayed, to be adjusted or altered using the light field display as a function of the user's pupil location. For instance, in some examples, users who would otherwise require corrective eyewear such as glasses or contact lenses, or again bifocals, may consume images produced by such devices, displays and methods in clear or improved focus without the use of such eyewear. Other light field display applications, such as 3D displays and the like, may also benefit from the solutions described herein, and thus, should be considered to fall within the general scope and nature of the present disclosure.

For example, some of the herein described embodiments provide for digital display devices, or devices encompassing such displays, for use by users having reduced visual acuity, whereby images ultimately rendered by such devices can be dynamically processed to accommodate the user's reduced visual acuity so that they may consume rendered images without the use of corrective eyewear, as would otherwise be required. As noted above, embodiments are not to be limited as such as the notions and solutions described herein may also be applied to other technologies in which a user's perception of an input image to be displayed can be altered or adjusted via the light field display.

Generally, digital displays as considered herein will comprise a set of image rendering pixels and an array of light-field shaping elements, also herein referred to interchangeably as a light field shaping layer, disposed at a preset distance therefrom so to controllably shape or influence a light field emanating therefrom. For instance, each light field shaping layer will be defined by an array of optical elements centered over a corresponding subset of the display's pixel array to optically influence a light field emanating therefrom and thereby govern a projection thereof from the display medium toward the user, for instance, providing some control over how each pixel or pixel group will be viewed by the viewer's eye(s). As will be further detailed below, arrayed optical elements may include, but are not limited to, lenslets, microlenses or other such diffractive optical elements that together form, for example, a lenslet array; pinholes or like apertures or windows that together form, for example, a parallax or like barrier; concentrically patterned barriers, e.g. cut outs and/or windows, such as a to define a Fresnel zone plate or optical sieve, for example, and that together form a diffractive optical barrier (as described, for example, in Applicant's co-pending U.S. application Ser. No. 15/910,908, the entire contents of which are hereby incorporated herein by reference); and/or a combination thereof, such as for example, a lenslet array whose respective lenses or lenslets are partially shadowed or barriered around a periphery thereof so to combine the refractive properties of the lenslet with some of the advantages provided by a pinhole barrier.

In operation, the display device will also generally invoke a hardware processor operable on image pixel (or subpixel) data for an image to be displayed to output corrected or adjusted image pixel data to be rendered as a function of a stored characteristic of the light field shaping layer (e.g. layer distance from display screen, distance between optical elements (pitch), absolute relative location of each pixel or subpixel to a corresponding optical element, properties of the optical elements (size, diffractive and/or refractive properties, etc.), or other such properties, and a selected vision correction or adjustment parameter related to the user's reduced visual acuity or intended viewing experience. While light field display characteristics will generally remain static for a given implementation (i.e. a given shaping layer will be used and set for each device irrespective of the user), image processing can, in some embodiments, be dynamically adjusted as a function of the user's visual acuity or intended application so to actively adjust a distance of a virtual image plane, or perceived image on the user's retinal plane given a quantified user eye focus or like optical aberration(s), induced upon rendering the corrected/adjusted image pixel data via the static optical layer, for example, or otherwise actively adjust image processing parameters as may be considered, for example, when implementing a viewer-adaptive pre-filtering algorithm or like approach (e.g. compressive light field optimization), so to at least in part govern an image perceived by the user's eye(s) given pixel or subpixel-specific light visible thereby through the layer.

Accordingly, a given device may be adapted to compensate for different visual acuity levels and thus accommodate different users and/or uses. For instance, a particular device may be configured to implement and/or render an interactive graphical user interface (GUI) that incorporates a dynamic vision correction scaling function that dynamically adjusts one or more designated vision correction parameter(s) in real-time in response to a designated user interaction therewith via the GUI. For example, a dynamic vision correction scaling function may comprise a graphically rendered scaling function controlled by a (continuous or discrete) user slide motion or like operation, whereby the GUI can be configured to capture and translate a user's given slide motion operation to a corresponding adjustment to the designated vision correction parameter(s) scalable with a degree of the user's given slide motion operation. These and other examples are described in Applicant's co-pending U.S. patent application Ser. No. 15/246,255, the entire contents of which are hereby incorporated herein by reference.

In general, a digital display device as considered herein may include, but is not limited to, smartphones, tablets, e-readers, watches, televisions, GPS devices, laptops, desktop computer monitors, televisions, smart televisions, handheld video game consoles and controllers, vehicular dashboard and/or entertainment displays, ticketing or shopping kiosks, point-of-sale (POS) systems, workstations, or the like.

Generally, the device will comprise a processing unit, a digital display, and internal memory. The display can be an LCD screen, a monitor, a plasma display panel, an LED or OLED screen, or any other type of digital display defined by a set of pixels for rendering a pixelated image or other like media or information. Internal memory can be any form of electronic storage, including a disk drive, optical drive, read-only memory, random-access memory, or flash memory, to name a few examples. For illustrative purposes, memory has stored in it a vision correction or image adjustment application and/or a predictive pupil tracking engine, though various methods and techniques may be implemented to provide computer-readable code and instructions for execution by the processing unit in order to process pixel data for an image to be rendered in producing corrected pixel data amenable to producing a corrected image accommodating the user's reduced visual acuity (e.g. stored and executable image correction application, tool, utility or engine, etc.). Other components of the electronic device may optionally include, but are not limited to, one or more rear and/or front-facing camera(s) (e.g. for onboard pupil tracking capabilities), pupil tracking light source, an accelerometer and/or other device positioning/orientation devices capable of determining the tilt and/or orientation of electronic device, or the like.

For example, the electronic device, or related environment (e.g. within the context of a desktop workstation, vehicular console/dashboard, gaming or e-learning station, multimedia display room, etc.) may include further hardware, firmware and/or software components and/or modules to deliver complementary and/or cooperative features, functions and/or services. For example, as previously noted, a pupil/eye tracking system may be integrally or cooperatively implemented to improve or enhance corrective image rendering by tracking a location of the user's eye(s)/pupil(s) (e.g. both or one, e.g. dominant, eye(s)) and adjusting light field corrections accordingly. For instance, the device may include, integrated therein or interfacing therewith, one or more eye/pupil tracking light sources, such as one or more infrared (IR) or near-IR (NIR) light source(s) to accommodate operation in limited ambient light conditions, leverage retinal retro-reflections, invoke corneal reflection, and/or other such considerations. For instance, different IR/NIR pupil tracking techniques may employ one or more (e.g. arrayed) directed or broad illumination light sources to stimulate retinal retro-reflection and/or corneal reflection in identifying and tracking a pupil location. Other techniques may employ ambient or IR/NIR light-based machine vision and facial recognition techniques to otherwise locate and track the user's eye(s)/pupil(s). To do so, one or more corresponding (e.g. visible, IR/NIR) cameras may be deployed to capture eye/pupil tracking signals that can be processed, using various image/sensor data processing techniques, to map a 3D location of the user's eye(s)/pupil(s). In the context of a mobile device, such as a mobile phone, such eye/pupil tracking hardware/software may be integral to the device, for instance, operating in concert with integrated components such as one or more front facing camera(s), onboard IR/NIR light source(s) and the like. In other user environments, such as in a vehicular environment, eye/pupil tracking hardware may be further distributed within the environment, such as dash, console, ceiling, windshield, mirror or similarly-mounted camera(s), light sources, etc.

Furthermore, the electronic device in this example will comprise a light field shaping layer (LFSL) or array of light field shaping elements overlaid atop a display thereof and spaced therefrom (e.g. via an integrated or distinct spacer) or other such means as may be readily apparent to the skilled artisan. For the sake of illustration, the following examples will be described within the context of a light field shaping layer defined, at least in part, by a lenslet array comprising an array of microlenses (also interchangeably referred to herein as lenslets) that are each disposed at a distance from a corresponding subset of image rendering pixels in an underlying digital display. It will be appreciated that while a light field shaping layer may be manufactured and disposed as a digital screen overlay, other integrated concepts may also be considered, for example, where light field shaping elements are integrally formed or manufactured within a digital screen's integral components such as a textured or masked glass plate, beam-shaping light sources or like component. Accordingly, each lenslet will predictively shape light emanating from these pixel subsets to at least partially govern light rays being projected toward the user by the display device. As noted above, other light field shaping layers may also be considered herein without departing from the general scope and nature of the present disclosure, whereby light field shaping will be understood by the person of ordinary skill in the art to reference measures by which light, that would otherwise emanate indiscriminately (i.e. isotropically) from each pixel group, is deliberately controlled to define predictable light rays that can be traced between the user and the device's pixels through the shaping layer.

For greater clarity, a light field is generally defined as a vector function that describes the amount of light flowing in every direction through every point in space. In other words, anything that produces or reflects light has an associated light field. The embodiments described herein produce light fields from an object that are not "natural" vector functions one would expect to observe from that object. This gives it the ability to emulate the "natural" light fields of objects that do not physically exist, such as a virtual display located far behind the light field display, which will be referred to now as the 'virtual image'. As noted in the examples below, in some embodiments, light field rendering may be adjusted to effectively generate a virtual image on a virtual image plane that is set at a designated distance from an input user pupil location, for example, so to effective push back, or move forward, a perceived image relative to the display device in accommodating a user's reduced visual acuity (e.g. minimum or maximum viewing distance). In yet other embodiments, light field rendering may rather or alternatively seek to map the input image on a retinal plane of the user, taking into account visual aberrations, so to adaptively adjust rendering of the input image on the display device to produce the mapped effect. Namely, where the unadjusted input image would otherwise typically come into focus in front of or behind the retinal plane (and/or be subject to other optical aberrations), this approach allows to map the intended image on the retinal plane and work therefrom to address designated optical aberrations accordingly. Using this approach, the device may further computationally interpret and compute virtual image distances tending toward infinity, for example, for extreme cases of presbyopia. This approach may also more readily allow, as will be appreciated by the below description, for adaptability to other visual aberrations that may not be as readily modeled using a virtual image and image plane implementation. In both of these examples, and like embodiments, the input image is digitally mapped to an adjusted image plane (e.g. virtual image plane or retinal plane) designated to provide the user with a designated image perception adjustment that at least partially addresses designated visual aberrations. Naturally, while visual aberrations may be addressed using these approaches, other visual effects may also be implemented using similar techniques.

Figure 8:
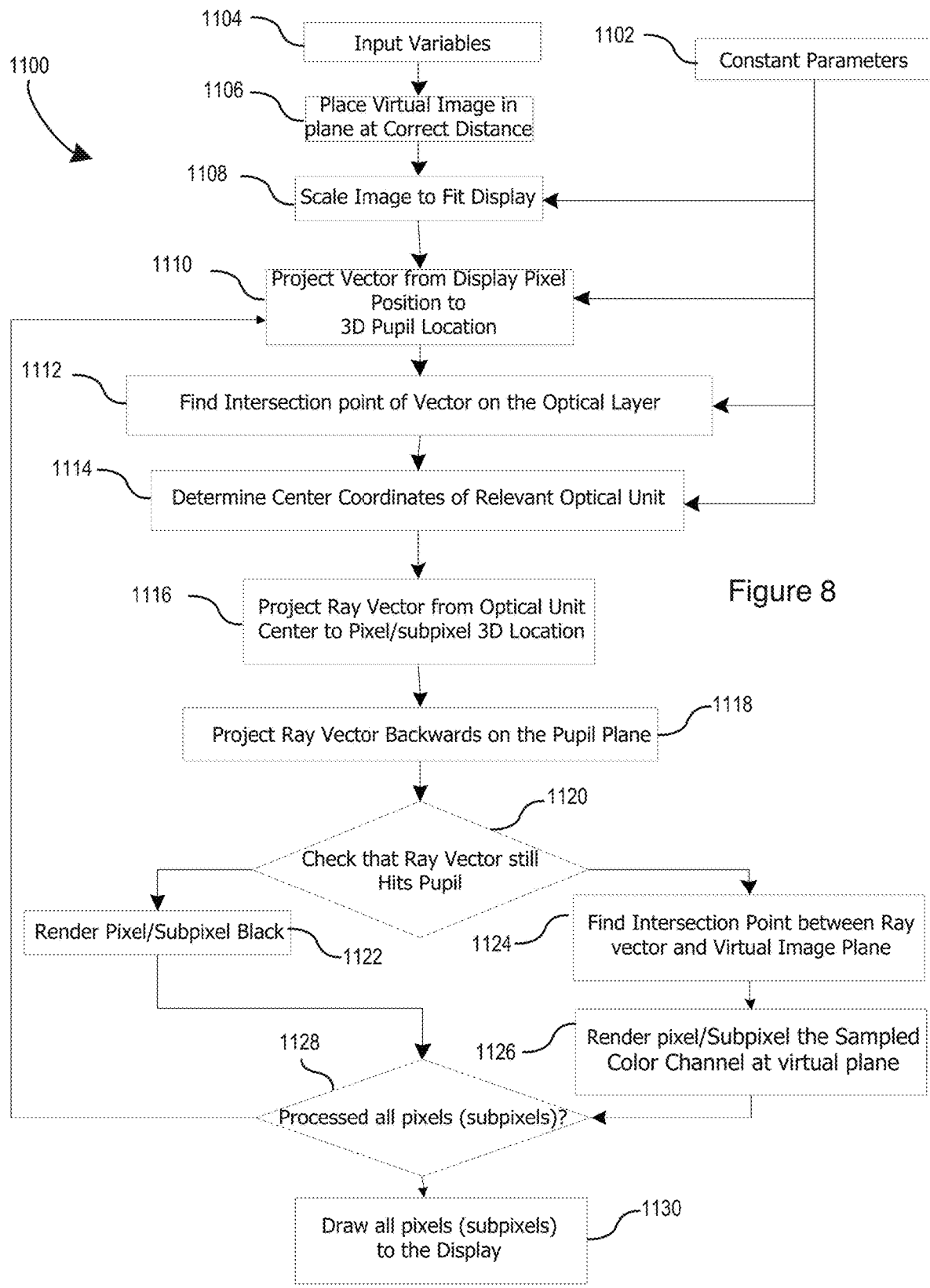
FIG. 8 is a process flow diagram of an illustrative ray-tracing rendering process, in accordance with one embodiment.
Figure 9:
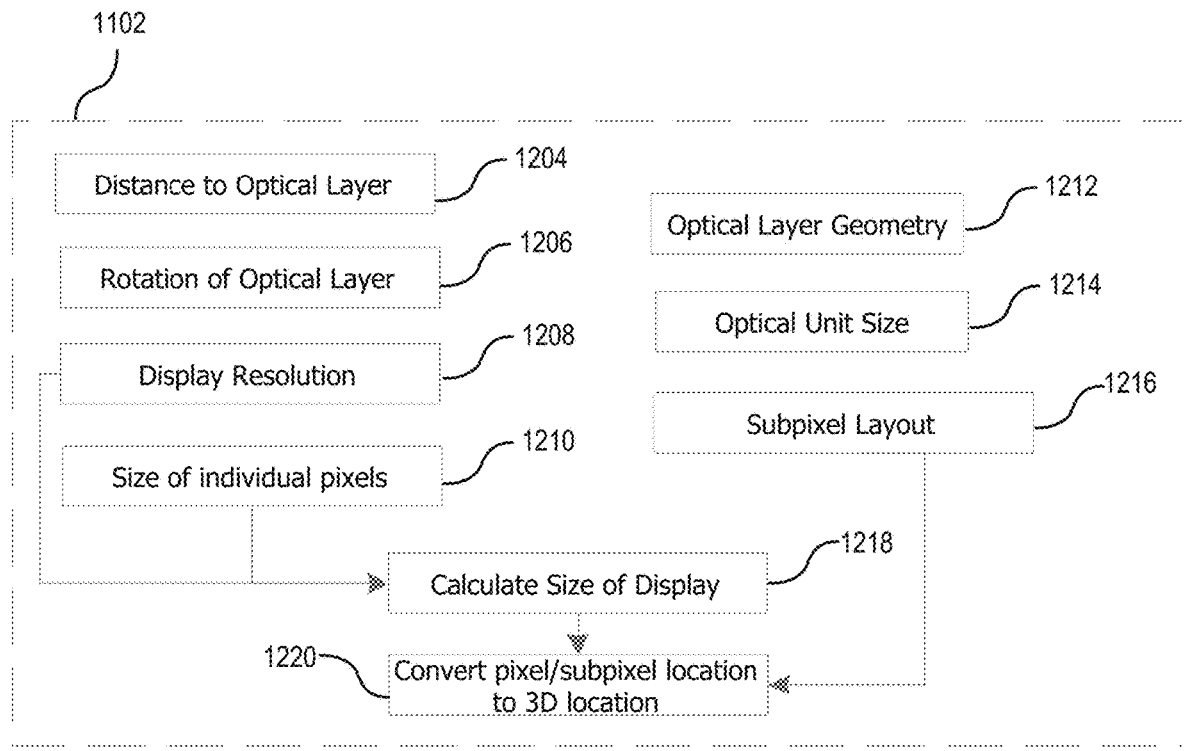
FIGS. 9 and 10 are process flow diagrams of exemplary input constant parameters and variables, respectively, for the ray-tracing rendering process of FIG. 8, in accordance with one embodiment.
Figure 10:
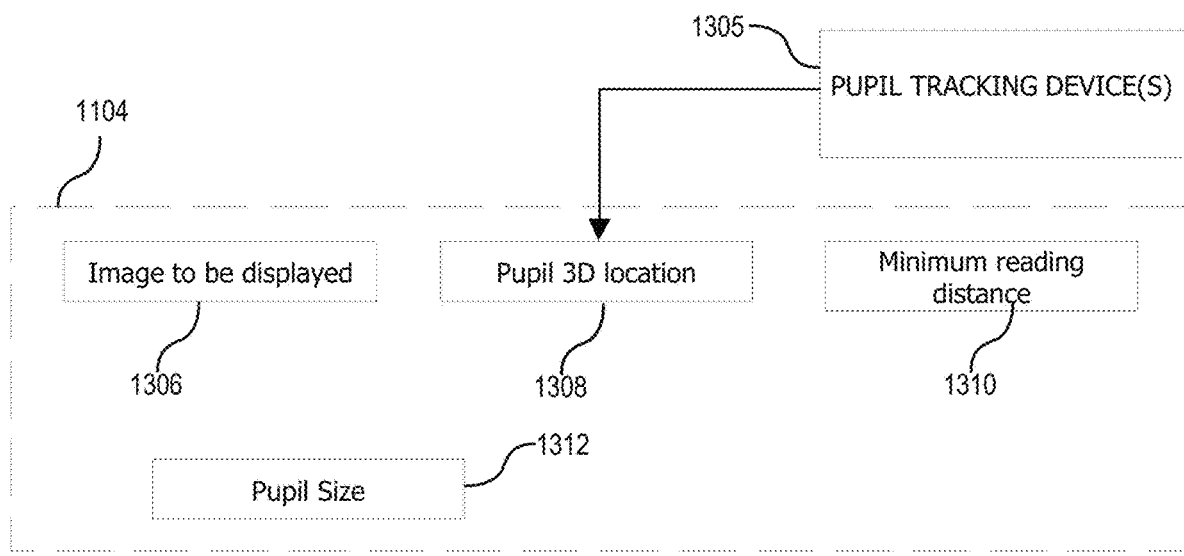

With reference to FIGS. 8 to 10, and in accordance with one embodiment, an exemplary, computationally implemented, ray-tracing method for rendering an adjusted image perception via a light field shaping layer (LFSL) or array of light field shaping elements, for example a computationally corrected image that accommodates for the user's reduced visual acuity, will now be described. In this exemplary embodiment, a set of constant parameters 1102 may be pre-determined. These may include, for example, any data that are not expected to significantly change during a user's viewing session, for instance, which are generally based on the physical and functional characteristics of the display for which the method is to be implemented, as will be explained below. Similarly, every iteration of the rendering algorithm may use a set of input variables 1104 which are expected to change either at each rendering iteration or at least between each user's viewing session.

As illustrated in FIG. 9, the list of constant parameters 1102 may include, without limitations, the distance 1204 between the display and the LFSL, the in-plane rotation angle 1206 between the display and LFSL frames of reference, the display resolution 1208, the size of each individual pixel 1210, the optical LFSL geometry 1212, the size of each optical element 1214 within the LFSL and optionally the subpixel layout 1216 of the display. Moreover, both the display resolution 1208 and the size of each individual pixel 1210 may be used to pre-determine both the absolute size of the display in real units (i.e. in mm) and the three-dimensional position of each pixel within the display. In some embodiments where the subpixel layout 1216 is available, the position within the display of each subpixel may also be pre-determined. These three-dimensional location/positions are usually calculated using a given frame of reference located somewhere within the plane of the display, for example a corner or the middle of the display, although other reference points may be chosen. Concerning the optical layer geometry 1212, different geometries may be considered, for example a hexagonal geometry such as the one shown in FIG. 10. Finally, by combining the distance 1204, the rotation angle 1206, and the geometry 1212 with the optical element size 1214, it is possible to similarly pre-determine the three-dimensional location/position of each optical element center with respect to the display's same frame of reference.

FIG. 10, meanwhile, illustratively lists an exemplary set of input variables 1104 for method 1100, which may include any input data fed into method 1100 that may reasonably change during a user's single viewing session, and may thus include without limitation: the image(s) to be displayed 1306 (e.g. pixel data such as on/off, colour, brightness, etc.) and the minimum reading distance 1310 (e.g. one or more parameters representative of the user's reduced visual acuity or condition). In some embodiments, the eye depth 1314 may also be used.

The image data 1306, for example, may be representative of one or more digital images to be displayed with the digital pixel display. This image may generally be encoded in any data format used to store digital images known in the art. In some embodiments, images 1306 to be displayed may change at a given framerate.

Following from the above-described embodiments, a further input variable includes the three-dimensional pupil location 1308, and optional pupil size 1312. As detailed above, the input pupil location in this sequence may include a current pupil location as output from a corresponding pupil tracking system, or a predicted pupil location, for example, when the process 1100 is implemented at a higher refresh rate than that otherwise available from the pupil tracking system, for instance, or if a pupil is moving sufficiently slowly that view zone re-rendering may not be necessary. As will be appreciated by the skilled artisan, the input pupil location 1308 may be provided by an external pupil tracking engine and/or device 1305, or again provided by an internal engine and/or integrated devices, depending the application and implementation at hand. For example, a self-contained digital display device such as a mobile phone, tablet, laptop computer, digital television, or the like may include integrated hardware to provide real time pupil tracking capabilities, such as an integrated camera and machine vision-based pupil tracking engine; integrated light source, camera and glint-based pupil tracking engine; and/or a combination thereof. In other embodiments or implementations, external pupil tracking hardware and/or firmware may be leveraged to provide a real time pupil location. For example, a vehicular dashboard, control or entertainment display may interface with an external camera(s) and/or pupil tracking hardware to produce a similar effect. Naturally, the integrated or distributed nature of the various hardware, firmware and/or software components required to execute the predictive pupil tracking functionalities described herein may vary for different applications, implementations and solution at hand.

The pupil location 1308, in one embodiment, is the three-dimensional coordinates of at least one the user's pupils' center with respect to a given reference frame, for example a point on the device or display. This pupil location 1308 may be derived from any eye/pupil tracking method known in the art. In some embodiments, the pupil location 1308 may be determined prior to any new iteration of the rendering algorithm, or in other cases, at a lower framerate. In some embodiments, only the pupil location of a single user's eye may be determined, for example the user's dominant eye (i.e. the one that is primarily relied upon by the user). In some embodiments, this position, and particularly the pupil distance to the screen may otherwise or additionally be rather approximated or adjusted based on other contextual or environmental parameters, such as an average or preset user distance to the screen (e.g. typical reading distance for a given user or group of users; stored, set or adjustable driver distance in a vehicular environment; etc.).

In the illustrated embodiment, the minimum reading distance 1310 is defined as the minimal focus distance for reading that the user's eye(s) may be able to accommodate (i.e. able to view without discomfort). In some embodiments, different values of the minimum reading distance 1310 associated with different users may be entered, for example, as can other adaptive vision correction parameters be considered depending on the application at hand and vision correction being addressed.

Figure 11A:
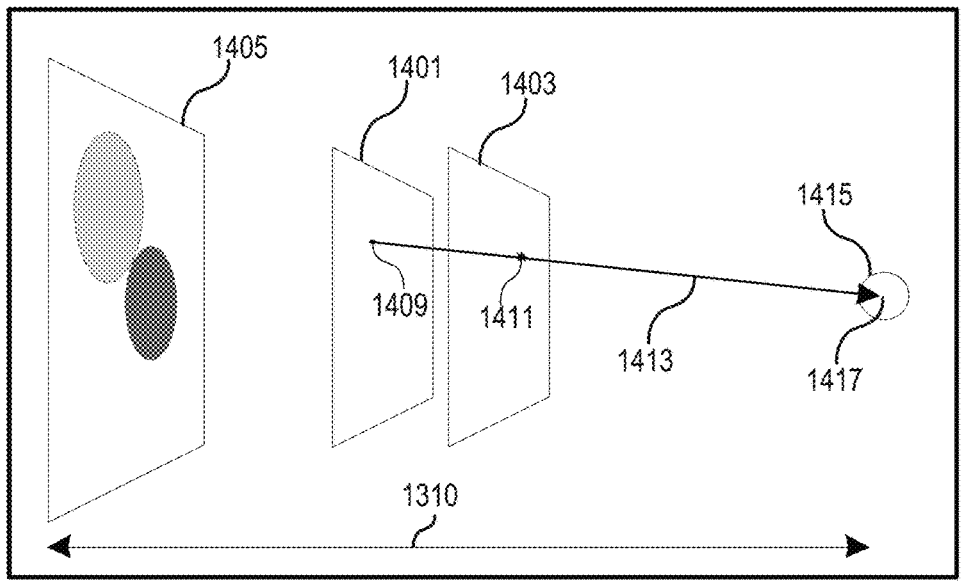
FIGS. 11A to 11C are schematic diagrams illustrating certain process steps of FIG. 8.
Figure 11B:
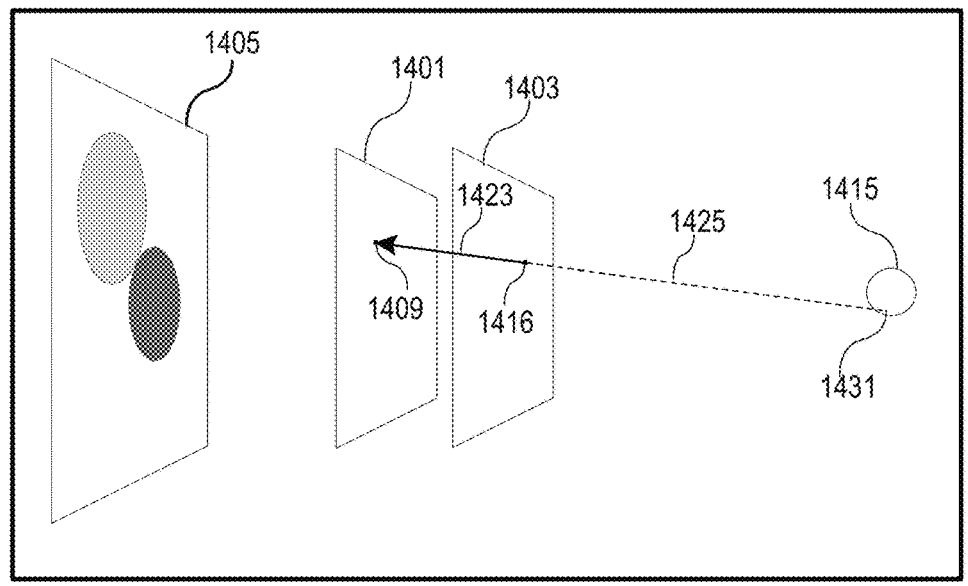
Figure 11C:
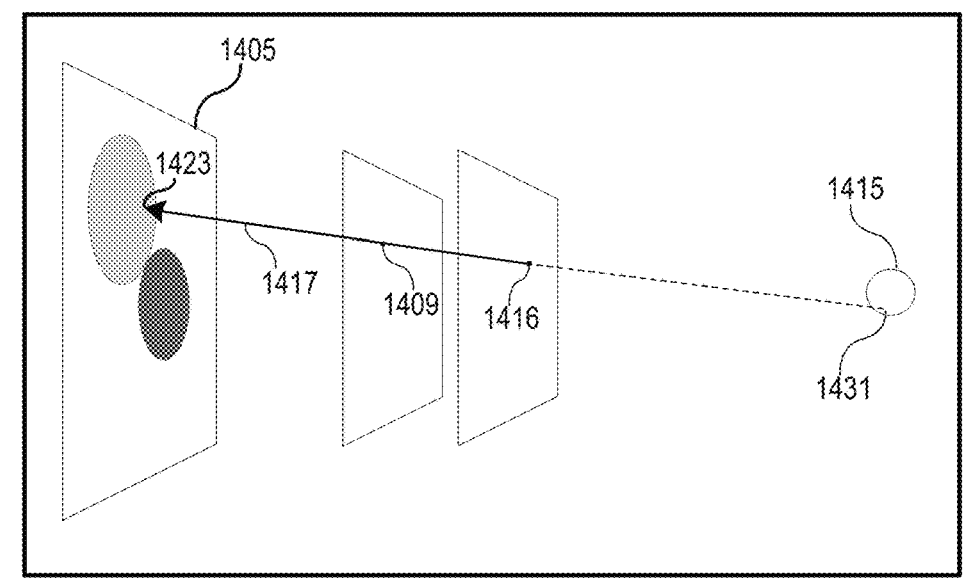

With added reference to FIGS. 11A to 11C, once parameters 1102 and variables 1104 have been set, the method of FIG. 13 then proceeds with step 1106, in which the minimum reading distance 1310 (and/or related parameters) is used to compute the position of a virtual (adjusted) image plane 1405 with respect to the device's display, followed by step 1108 wherein the size of image 1306 is scaled within the image plane 1405 to ensure that it correctly fills the pixel display 1401 when viewed by the distant user. This is illustrated in FIG. 11A, which shows a diagram of the relative positioning of the user's pupil 1415, the light field shaping layer 1403, the pixel display 1401 and the virtual image plane 1405. In this example, the size of image 1306 in image plane 1405 is increased to avoid having the image as perceived by the user appear smaller than the display's size.

An exemplary ray-tracing methodology is described in steps 1110 to 1128 of FIG. 8, at the end of which the output color of each pixel of pixel display 1401 is known so as to virtually reproduce the light field emanating from an image 1306 positioned at the virtual image plane 1405. In FIG. 8, these steps are illustrated in a loop over each pixel in pixel display 1401, so that each of steps 1110 to 1126 describes the computations done for each individual pixel. However, in some embodiments, these computations need not be executed sequentially, but rather, steps 1110 to 1128 may executed in parallel for each pixel or a subset of pixels at the same time. Indeed, as will be discussed below, this exemplary method is well suited to vectorization and implementation on highly parallel processing architectures such as GPUs.

As illustrated in FIGS. 11A to 11C, in step 1110, for a given pixel 1409 in pixel display 1401, a trial vector 1413 is first generated from the pixel's position to the (actual or predicted) center position 1417 of pupil 1415. This is followed in step 1112 by calculating the intersection point 1411 of vector 1413 with the LFSL 1403.

The method then finds, in step 1114, the coordinates of the center 1416 of the LFSL optical element closest to intersection point 1411. Once the position of the center 1416 of the optical element is known, in step 1116, a normalized unit ray vector is generated from drawing and normalizing a vector 1423 drawn from center position 1416 to pixel 1409. This unit ray vector generally approximates the direction of the light field emanating from pixel 1409 through this particular light field element, for instance, when considering a parallax barrier aperture or lenslet array (i.e. where the path of light travelling through the center of a given lenslet is not deviated by this lenslet). Further computation may be required when addressing more complex light shaping elements, as will be appreciated by the skilled artisan. The direction of this ray vector will be used to find the portion of image 1306, and thus the associated color, represented by pixel 1409. But first, in step 1118, this ray vector is projected backwards to the plane of pupil 1415, and then in step 1120, the method verifies that the projected ray vector 1425 is still within pupil 1415 (i.e. that the user can still "see" it). Once the intersection position, for example location 1431 in FIG. 11B, of projected ray vector 1425 with the pupil plane is known, the distance between the pupil center 1417 and the intersection point 1431 may be calculated to determine if the deviation is acceptable, for example by using a pre-determined pupil size and verifying how far the projected ray vector is from the pupil center.

If this deviation is deemed to be too large (i.e. light emanating from pixel 1409 channeled through optical element 1416 is not perceived by pupil 1415), then in step 1122, the method flags pixel 1409 as unnecessary and to simply be turned off or render a black color. Otherwise, as shown in FIG. 11C, in step 1124, the ray vector is projected once more towards virtual image plane 1405 to find the position of the intersection point 1423 on image 1306. Then in step 1126, pixel 1409 is flagged as having the color value associated with the portion of image 1306 at intersection point 1423.

In some embodiments, method 1100 is modified so that at step 1120, instead of having a binary choice between the ray vector hitting the pupil or not, one or more smooth interpolation function (i.e. linear interpolation, Hermite interpolation or similar) are used to quantify how far or how close the intersection point 1431 is to the pupil center 1417 by outputting a corresponding continuous value between 1 or 0. For example, the assigned value is equal to 1 substantially close to pupil center 1417 and gradually change to 0 as the intersection point 1431 substantially approaches the pupil edges or beyond. In this case, the branch containing step 1122 is ignored and step 1220 continues to step 1124. At step 1126, the pixel color value assigned to pixel 1409 is chosen to be somewhere between the full color value of the portion of image 1306 at intersection point 1423 or black, depending on the value of the interpolation function used at step 1120 (1 or 0).

In yet other embodiments, pixels found to illuminate a designated area around the pupil may still be rendered, for example, to produce a buffer zone to accommodate small movements in pupil location, for example, or again, to address potential inaccuracies, misalignments or to create a better user experience.

In some embodiments, steps 1118, 1120 and 1122 may be avoided completely, the method instead going directly from step 1116 to step 1124. In such an exemplary embodiment, no check is made that the ray vector hits the pupil or not, but instead the method assumes that it always does.

Once the output colors of all pixels have been determined, these are finally rendered in step 1130 by pixel display 1401 to be viewed by the user, therefore presenting a light field corrected image. In the case of a single static image, the method may stop here. However, new input variables may be entered and the image may be refreshed at any desired frequency, for example because the user's pupil moves as a function of time and/or because instead of a single image a series of images are displayed at a given framerate.

With reference to FIGS. 12 and 13A to 13D, and in accordance with one embodiment, another exemplary computationally implemented ray-tracing method for rendering an adjusted image via the light field shaping layer (LFSL) that accommodates for the user's reduced visual acuity, for example, will now be described. In this embodiment, the adjusted image portion associated with a given pixel/sub-pixel is computed (mapped) on the retina plane instead of the virtual image plane considered in the above example, again in order to provide the user with a designated image perception adjustment. Therefore, the currently discussed exemplary embodiment shares some steps with the method of FIG. 8. Indeed, a set of constant parameters 1402 may also be pre-determined. These may include, for example, any data that are not expected to significantly change during a user's viewing session, for instance, which are generally based on the physical and functional characteristics of the display for which the method is to be implemented, as will be explained below. Similarly, every iteration of the rendering algorithm may use a set of input variables 1404 which are expected to change either at each rendering iteration or at least between each user viewing session. The list of possible variables and constants is substantially the same as the one disclosed in FIGS. 9 and 10 and will thus not be replicated here.

Once parameters 1402 and variables 1404 have been set, this second exemplary ray-tracing methodology proceeds from steps 1910 to 1936, at the end of which the output color of each pixel of the pixel display is known so as to virtually reproduce the light field emanating from an image perceived to be positioned at the correct or adjusted image distance, in one example, so to allow the user to properly focus on this adjusted image (i.e. having a focused image projected on the user's retina) despite a quantified visual aberration. In FIG. 12, these steps are illustrated in a loop over each pixel in pixel display 1401, so that each of steps 1910 to 1934 describes the computations done for each individual pixel. However, in some embodiments, these computations need not be executed sequentially, but rather, steps 1910 to 1934 may be executed in parallel for each pixel or a subset of pixels at the same time. Indeed, as will be discussed below, this second exemplary method is also well suited to vectorization and implementation on highly parallel processing architectures such as GPUs.

Referencing once more FIG. 11A, in step 1910 (as in step 1110), for a given pixel in pixel display 1401, a trial vector 1413 is first generated from the pixel's position to (actual or predicted) pupil center 1417 of the user's pupil 1415. This is followed in step 1912 by calculating the intersection point of vector 1413 with optical layer 1403.

From there, in step 1914, the coordinates of the optical element center 1416 closest to intersection point 1411 are determined. This step may be computationally intensive and will be discussed in more depth below. As shown in FIG. 11B, once the position of the optical element center 1416 is known, in step 1916, a normalized unit ray vector is generated from drawing and normalizing a vector 1423 drawn from optical element center 1416 to pixel 1409. This unit ray vector generally approximates the direction of the light field emanating from pixel 1409 through this particular light field element, for instance, when considering a parallax barrier aperture or lenslet array (i.e. where the path of light travelling through the center of a given lenslet is not deviated by this lenslet). Further computation may be required when addressing more complex light shaping elements, as will be appreciated by the skilled artisan. In step 1918, this ray vector is projected backwards to pupil 1415, and then in step 1920, the method ensures that the projected ray vector 1425 is still within pupil 1415 (i.e. that the user can still "see" it). Once the intersection position, for example location 1431 in FIG. 11B, of projected ray vector 1425 with the pupil plane is known, the distance between the pupil center 1417 and the intersection point 1431 may be calculated to determine if the deviation is acceptable, for example by using a pre-determined pupil size and verifying how far the projected ray vector is from the pupil center.

Now referring to FIGS. 13A to 13D, steps 1921 to 1929 of method 1900 will be described. Once optical element center 1416 of the relevant optical unit has been determined, at step 1921, a vector 2004 is drawn from optical element center 1416 to (actual or predicted) pupil center 1417. Then, in step 1923, vector 2004 is projected further behind the pupil plane onto focal plane 2006 (location where any light rays originating from optical layer 1403 would be focused by the eye's lens) to locate focus point 2008. For a user with perfect vision, focal plane 2006 would be located at the same location as retina plane 2010, but in this example, focal plane 2006 is located behind retina plane 2006, which would be expected for a user with some form of farsightedness. The position of focal plane 2006 may be derived from the user's minimum reading distance 1310, for example, by deriving therefrom the focal length of the user's eye. Other manually input or computationally or dynamically adjustable means may also or alternatively be considered to quantify this parameter.

The skilled artisan will note that any light ray originating from optical element center 1416, no matter its orientation, will also be focused onto focus point 2008, to a first approximation. Therefore, the location on retina plane (2012) onto which light entering the pupil at intersection point 1431 will converge may be approximated by drawing a straight line between intersection point 1431 where ray vector 1425 hits the pupil 1415 and focus point 2008 on focal plane 2006. The intersection of this line with retina plane 2010 (retina image point 2012) is thus the location on the user's retina corresponding to the image portion that will be reproduced by corresponding pixel 1409 as perceived by the user. Therefore, by comparing the relative position of retina point 2012 with the overall position of the projected image on the retina plane 2010, the relevant adjusted image portion associated with pixel 1409 may be computed.

To do so, at step 1927, the corresponding projected image center position on retina plane 2010 is calculated. Vector 2016 is generated originating from the center position of display 1401 (display center position 2018) and passing through pupil center 1417. Vector 2016 is projected beyond the pupil plane onto retina plane 2010, wherein the associated intersection point gives the location of the corresponding retina image center 2020 on retina plane 2010. The skilled technician will understand that step 1927 could be performed at any moment prior to step 1929, once the relative pupil center location 1417 is known in input variables step 1904. Once image center 2020 is known, one can then find the corresponding image portion of the selected pixel/subpixel at step 1929 by calculating the x/y coordinates of retina image point 2012 relative to retina image center 2020 on the retina, scaled to the x/y retina image size 2031.

Figure 13A:
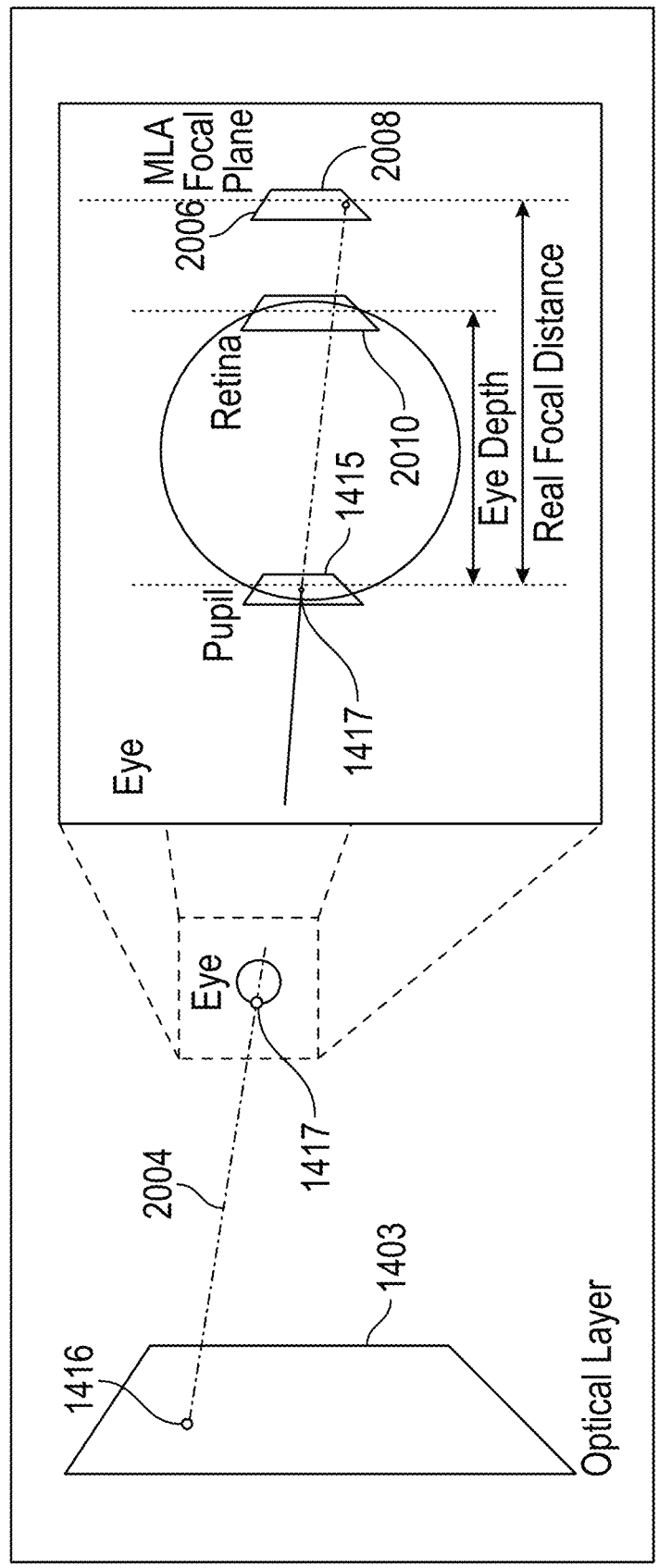
FIGS. 13A to 13D are schematic diagrams illustrating certain process steps of FIG. 12.
Figure 13B:
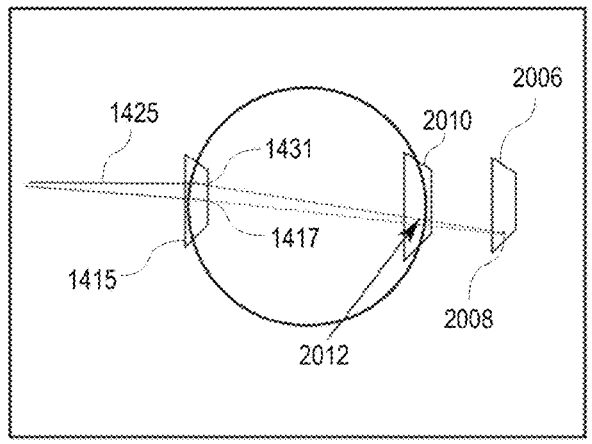
Figure 13C:
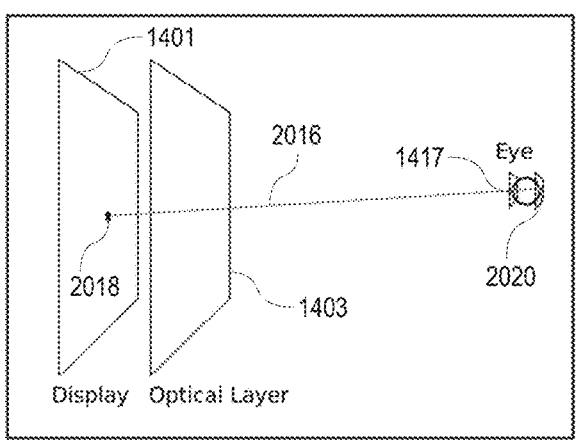
Figure 13D:
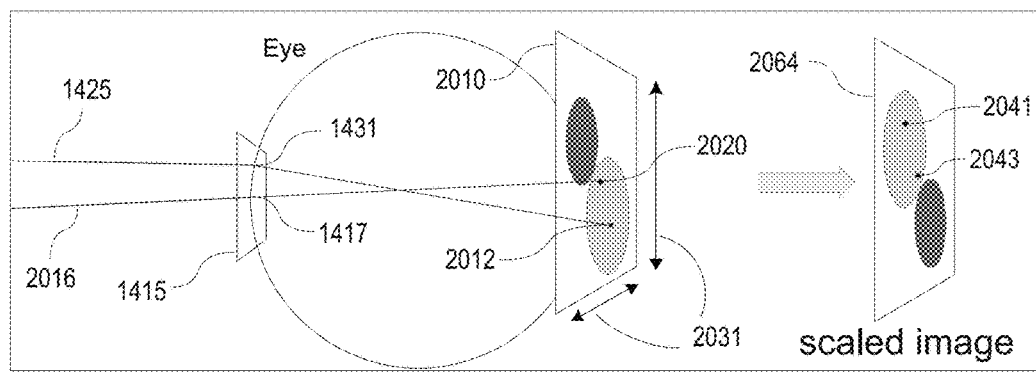

This retina image size 2031 may be computed by calculating the magnification of an individual pixel on retina plane 2010, for example, which may be approximately equal to the x or y dimension of an individual pixel multiplied by the eye depth 1314 and divided by the absolute value of the distance to the eye (i.e. the magnification of pixel image size from the eye lens). Similarly, for comparison purposes, the input image is also scaled by the image x/y dimensions to produce a corresponding scaled input image 2064. Both the scaled input image and scaled retina image should have a width and height between −0.5 to 0.5 units, enabling a direct comparison between a point on the scaled retina image 2010 and the corresponding scaled input image 2064, as shown in FIG. 13D.

From there, the image portion position 2041 relative to retina image center position 2043 in the scaled coordinates (scaled input image 2064) corresponds to the inverse (because the image on the retina is inverted) scaled coordinates of retina image point 2012 with respect to retina image center 2020. The associated color with image portion position 2041 is therefrom extracted and associated with pixel 1409.

In some embodiments, method 1900 may be modified so that at step 1920, instead of having a binary choice between the ray vector hitting the pupil or not, one or more smooth interpolation function (i.e. linear interpolation, Hermite interpolation or similar) are used to quantify how far or how close the intersection point 1431 is to the pupil center 1417 by outputting a corresponding continuous value between 1 or 0. For example, the assigned value is equal to 1 substantially close to pupil center 1417 and gradually change to 0 as the intersection point 1431 substantially approaches the pupil edges or beyond. In this case, the branch containing step 1122 is ignored and step 1920 continues to step 1124. At step 1931, the pixel color value assigned to pixel 1409 is chosen to be somewhere between the full color value of the portion of image 1306 at intersection point 1423 or black, depending on the value of the interpolation function used at step 1920 (1 or 0).

In yet other embodiments, pixels found to illuminate a designated area around the pupil may still be rendered, for example, to produce a buffer zone to accommodate small movements in pupil location, for example, or again, to address potential inaccuracies or misalignments.

Once the output colors of all pixels in the display have been determined (check at step 1934 is true), these are finally rendered in step 1936 by pixel display 1401 to be viewed by the user, therefore presenting a light field corrected image. In the case of a single static image, the method may stop here. However, new input variables may be entered and the image may be refreshed at any desired frequency, for example because the user's pupil moves as a function of time and/or because instead of a single image a series of images are displayed at a given framerate.

As will be appreciated by the skilled artisan, selection of the adjusted image plane onto which to map the input image in order to adjust a user perception of this input image allows for different ray tracing approaches to solving a similar challenge, that is of creating an adjusted image using the light field display that can provide an adjusted user perception, such as addressing a user's reduce visual acuity. While mapping the input image to a virtual image plane set at a designated minimum (or maximum) comfortable viewing distance can provide one solution, the alternate solution may allow accommodation of different or possibly more extreme visual aberrations. For example, where a virtual image is ideally pushed to infinity (or effectively so), computation of an infinite distance becomes problematic. However, by designating the adjusted image plane as the retinal plane, the illustrative process of FIG. 12 can accommodate the formation of a virtual image effectively set at infinity without invoking such computational challenges. Likewise, while first order focal length aberrations are illustratively described with reference to FIG. 12, higher order or other optical anomalies may be considered within the present context, whereby a desired retinal image is mapped out and traced while accounting for the user's optical aberration(s) so to compute adjusted pixel data to be rendered in producing that image. These and other such considerations should be readily apparent to the skilled artisan.

While the computations involved in the above described ray-tracing algorithms (steps 1110 to 1128 of FIG. 8 or steps 1920 to 1934 of FIG. 12) may be done on general CPUs, it may be advantageous to use highly parallel programming schemes to speed up such computations. While in some embodiments, standard parallel programming libraries such as Message Passing Interface (MPI) or OPENMP may be used to accelerate the light field rendering via a general-purpose CPU, the light field computations described above are especially tailored to take advantage of graphical processing units (GPU), which are specifically tailored for massively parallel computations. Indeed, modern GPU chips are characterized by the very large number of processing cores, and an instruction set that is commonly optimized for graphics. In typical use, each core is dedicated to a small neighborhood of pixel values within an image, e.g., to perform processing that applies a visual effect, such as shading, fog, affine transformation, etc. GPUs are usually also optimized to accelerate exchange of image data between such processing cores and associated memory, such as RGB frame buffers. Furthermore, smartphones are increasingly being equipped with powerful GPUs to speed the rendering of complex screen displays, e.g., for gaming, video, and other image-intensive applications. Several programming frameworks and languages tailored for programming on GPUs include, but are not limited to, CUDA, OpenCL, OpenGL Shader Language (GLSL), High-Level Shader Language (HLSL) or similar. However, using GPUs efficiently may be challenging and thus require creative steps to leverage their capabilities, as will be discussed below.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become apparent to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims. Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the disclosure.

What is claimed is:

1. A computer-implemented method, automatically implemented by one or more digital processors, for reducing jitteriness or increasing stability in a perceived light field image projected via a light field display, the method comprising:
    sequentially acquiring a user pupil location;
    digitally computing from at least some said sequentially acquired user pupil location a velocity of said user pupil location over time;
    digitally comparing said velocity with a designated threshold pupil velocity, wherein velocities below said designated threshold are associated with a relatively fixated state;
    digitally rendering the light field image via the light field display in accordance with a maintained spatially-defined light field viewing zone geometry digitally defined in respect of a previously acquired user pupil location to project the light field image within a maintained spatially-defined light field viewing zone in accordance with said previously acquired user pupil location so to reduce jitteriness or increase stability of the perceived light field image, unless said velocity is above said designated threshold pupil velocity; and
    upon said velocity exceeding said designated threshold pupil velocity, digitally adjusting a rendering geometry of the light field image via the light field display so to correspondingly adjust said maintained spatially-defined light field viewing zone geometry to project the light field image within an adjusted spatially-defined light field viewing zone in accordance with a newly acquired user pupil location.

2. The computer-implemented method of claim 1, further comprising digitally adjusting said rendering geometry of the light field image via the light field display so to correspondingly adjust said maintained spatially-defined light field viewing zone geometry to correspond to a function of said newly acquired user pupil location upon a designated condition for movement of said maintained spatially-defined light field viewing zone geometry being met.

3. The computer-implemented method of claim 2, wherein said designated condition for movement of said maintained spatially-defined light field viewing zone geometry comprises at least one of said user pupil location crossing a defined boundary of said maintained spatially-defined light field viewing zone geometry, said maintained light field viewing zone geometry remaining static for a prescribed period of time, or said velocity is greater than a distinct predetermined threshold.

4. The computer-implemented method of claim 2, wherein said function is an interpolation of said newly acquired user pupil location and said maintained spatially-defined light field viewing zone geometry.

5. The computer-implemented method of claim 2, wherein said function is a function of time since said designated condition for movement was met.

6. The computer-implemented method of claim 4, where said interpolation is calculated for a designated period of time after said designated condition was met.

7. The computer-implemented method of claim 6, wherein said designated period of time is between about 0.02 s and 1 s.

8. The computer-implemented method of claim 1, wherein said threshold velocity is between 0.02 m/s and 1 m/s.

9. The computer-implemented method of claim 8, wherein said threshold velocity is approximately 0.1 m/s.

10. The computer-implemented method of claim 1, wherein said digitally rendering the light field image via the light field display comprises:
    digitally mapping a digital image on an adjusted image plane designated to provide the user with a designated image perception adjustment;
    associating adjusted image pixel data with at least some of said pixels according to said mapping; and
    rendering said adjusted image pixel data via said pixels thereby rendering said light field image corresponding to a perceptively adjusted version of the digital image.

11. A non-transitory computer-readable medium having instructions stored thereon to be automatically implemented by one or more processors to reduce jitteriness or increase stability in a perceived light field image projected via a light field display by:

sequentially acquiring a user pupil location;
digitally computing from at least some said sequentially acquired user pupil location a velocity of said user pupil location over time;
digitally comparing said velocity with a designated threshold pupil velocity, wherein velocities below said designated threshold are associated with a relatively fixated state;
digitally rendering the light field image via the light field display in accordance with a maintained spatially-defined light field viewing zone geometry digitally defined in respect of a previously acquired user pupil location to project the light field image within a maintained spatially-defined light field viewing zone in accordance with said previously acquired user pupil location so to reduce jitteriness or increase stability of the perceived light field image, unless said velocity is above said designated threshold pupil velocity; and
upon said velocity exceeding said designated threshold pupil velocity, digitally adjusting a rendering geometry of the light field image via the light field display so to correspondingly adjust said maintained spatially-defined light field viewing zone geometry to project the light field image within an adjusted spatially-defined light field viewing zone in accordance with a newly acquired user pupil location.

12. The non-transitory computer-readable medium of claim 11, further comprising digitally adjusting said rendering geometry of the light field image via the light field display so to correspondingly adjust said spatially-defined light field viewing zone geometry to correspond to a function of said newly acquired user pupil location upon a designated condition for movement of said spatially-defined light field viewing zone geometry is met.

13. The non-transitory computer-readable medium of claim 12, wherein said designated condition for movement of said spatially-defined light field viewing zone geometry comprises at least one of said user pupil location crossing a defined boundary of said maintained spatially-defined light field viewing zone geometry, said maintained spatially-defined light field viewing zone geometry remaining static for a prescribed period of time, or said velocity is greater than a distinct predetermined threshold.

14. The non-transitory computer-readable medium of claim 12, wherein said function is an interpolation of said newly acquired user pupil location and said maintained spatially-defined light field viewing zone geometry.

15. The non-transitory computer-readable medium of claim 12, wherein said function is a function of time since said designated condition for movement was met.

16. The non-transitory computer-readable medium of claim 14, where said interpolation is calculated for a designated period of time after said designated condition was met.

17. The non-transitory computer-readable medium of claim 16, wherein said designated period of time is between about 0.02 s and 1 s.

18. The non-transitory computer-readable medium of claim 11, wherein said threshold velocity is between 0.02 m/s and 1 m/s.

19. The non-transitory computer-readable medium of claim 18, wherein said threshold velocity is approximately 0.1 m/s.

20. The non-transitory computer-readable medium of claim 11, wherein said digitally rendering the light field image via the light field display comprises instructions for:
digitally mapping a digital image on an adjusted image plane designated to provide the user with a designated image perception adjustment;
associating adjusted image pixel data with at least some of said pixels according to said mapping; and
rendering said adjusted image pixel data via said pixels thereby rendering said light field image corresponding to a perceptively adjusted version of the digital image.

21. A digital display device operable to automatically adjust a light field image to be rendered thereon, the device comprising:
a light field display;
a hardware processor; and
a pupil tracking engine operable by said hardware processor to automatically:
receive as input sequential user pupil locations;
digitally compute from at least some said sequential user pupil locations a velocity of said user pupil location over time; and
digitally compare said velocity with a designated threshold pupil velocity, wherein velocities below said designated threshold are associated with a relatively fixated state;
wherein said hardware processor is operable to reduce jitteriness or increase stability in a perceived light field image by:
digitally rendering the light field image via the light field display in accordance with a maintained spatially-defined light field viewing zone geometry digitally defined in respect of a previously acquired user pupil location to project the light field image within a maintained spatially defined light field viewing zone in accordance with said previously acquired user pupil location so to reduce jitteriness or increase stability of the perceived light field image, unless said velocity is above said designated threshold pupil velocity; and
upon said velocity exceeding said designated threshold pupil velocity, digitally adjusting a rendering geometry of the light field image via the light field display so to correspondingly adjust said maintained spatially-defined light field viewing zone geometry to project the light field image within an adjusted spatially-defined light field viewing zone in accordance with a newly acquired user pupil location.

22. The digital display device of claim 21, further comprising digitally adjusting said rendering geometry of the light field image via the light field display so to correspondingly adjust said maintained spatially-defined light field viewing zone geometry to correspond to a function of said newly acquired user pupil location upon a designated condition for movement of said maintained spatially-defined light field viewing zone geometry is met.

23. The digital display device of claim 22, wherein said designated condition for movement of said maintained spatially-defined viewing zone geometry comprises at least one of said user pupil location crossing a defined boundary of said maintained spatially-defined light field viewing zone geometry, said maintained spatially-defined light field viewing zone geometry remaining static for a prescribed period of time, or said velocity is greater than a distinct predetermined threshold.

24. The digital display device of claim 22, wherein said function is an interpolation of said newly acquired user pupil location and said maintained spatially-defined light field viewing zone geometry.

25. The digital display device of claim 22, wherein said function is a function of time since said designated condition for movement was met.

26. The digital display device of claim 24, where said interpolation is calculated for a designated period of time after said designated condition was met.

27. The digital display of claim 21, wherein said hardware processor is operable to digitally render the light field image via the light field display by:
- digitally mapping a digital image on an adjusted image plane designated to provide the user with a designated image perception adjustment;
- associating adjusted image pixel data with at least some of said pixels according to said mapping; and
- rendering said adjusted image pixel data via said pixels thereby rendering said light field image corresponding to a perceptively adjusted version of the digital image.

* * * * *